US006197301B1

(12) United States Patent
Flavell et al.

(10) Patent No.: US 6,197,301 B1
(45) Date of Patent: Mar. 6, 2001

(54) COMPOSITIONS AND METHODS FOR THE PREVENTION AND DIAGNOSIS OF LYME DISEASE

(75) Inventors: Richard A. Flavell, Killingworth; Fred S. Kantor, Orange; Stephen W. Barthold, Madison; Erol Fikrig, Guilford, all of CT (US)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 08/455,829

(22) Filed: May 31, 1995

Related U.S. Application Data

(62) Division of application No. 08/320,161, filed on Oct. 7, 1994, now Pat. No. 5,747,294, which is a continuation of application No. 07/682,355, filed on Apr. 8, 1991, now abandoned, which is a continuation-in-part of application No. 07/602,551, filed on Oct. 26, 1990, now abandoned, which is a continuation-in-part of application No. 07/538,969, filed on Jun. 15, 1990, now abandoned.

(51) Int. Cl.$^7$ .......................... A61K 38/16; A61K 39/02
(52) U.S. Cl. ..................... 424/190.1; 424/192.1; 424/197.11; 424/234.1; 435/7.32; 435/810; 435/975; 436/536; 514/2; 530/324; 530/350; 530/403; 530/825
(58) Field of Search ..................... 530/300, 350, 530/324, 403, 825; 435/172.3, 91.1, 7.32, 810, 975; 536/23.7; 424/184.1, 185.1, 192.1, 190.1, 197.11; 436/536; 514/2

(56) References Cited

U.S. PATENT DOCUMENTS

| 4,721,617 | 1/1988 | Johnson . |
| 4,754,065 | 6/1988 | Levenson et al. . |
| 4,800,159 | 1/1989 | Mullis et al. . |
| 4,816,564 | 3/1989 | Ellis et al. . |
| 4,888,280 | * 12/1989 | Palmer et al. ................ 435/69.7 |
| 4,963,483 | 10/1990 | Ellis et al. . |
| 5,178,859 | 1/1993 | Simon et al. . |
| 5,227,293 | * 7/1993 | Stengelin et al. ............. 435/69.7 |
| 5,403,718 | 4/1995 | Dorward et al. . |
| 5,523,089 | * 6/1996 | Bergstrom et al. ........... 424/262.1 |
| 5,688,512 | * 11/1997 | Bergstrom et al. ........... 424/234.1 |

FOREIGN PATENT DOCUMENTS

| 2025597 | 3/1991 | (CA) . |
| 421725 | 4/1991 | (EP) . |
| WO 90/04411 | 5/1990 | (WO) . |

OTHER PUBLICATIONS

A.G. Barbour, "Plasmid Analysis of *Borrelia Burgdorferi*, The Lyme Disease Agent", *J. Clin. Micro.* 26, pp. 475–478 (1988).

A.G. Barbour and C.F. Garon, "Linear Plasmids Of The Bacterium *Borrelia Burgdorferi* Have Covalently Closed Ends", *Science*, 237, pp. 409–411 (1987).

A.G. Barbour et al., "A Borrelia–Specific Monoclonal Antibody Binds To A Flagellar Epitope", *Infect. Immun.*, 52, pp. 549–554 (1986).

A.G. Barbour et al., "Variation In A Major Surface Protein Of Lyme Disease Spirochetes", *Infect. Immun.*, 45, pp. 94–100 (1984).

A.G. Barbour et al., "Lyme Disease Spirochetes And Ixodid Tick Spirochetes Share A Common Surface Antigenic Determinant Defined By A Monoclonal Antibody", *Infect. Immun.*, 41, pp. 795–804 (1983).

A.G. Barbour et al., "Heterogeneity Of Major Proteins In Lyme Disease Borreliae: A Molecular Analysis Of North American And European Isolates", *J. Infect. Dis.*, 152, pp. 478–484 (1985).

S.W. Barthold et al., "Lyme Borreliosis In Selected Strains And Ages Of Laboratory Mice", *J. Infect. Dis.*, 162, pp. 133–138 (1990).

J.L. Benach et al., "A Murine IgM Monoclonal Antibody Binds An Antigenic Determinant In Outer Surface Protein A, An Immunodominant Basic Protein Of The Lyme Disease Spirochete", *J. Immun.*, 140, pp. 265–272 (1988).

J.L. Benach et al., "Biological Activity of *Borrelia Burgdorferi* Antigens", *Ann. NY Acad. Sci.*, 539, pp. 115–125 (1988).

B.W. Berger et al., "Isolation And Characterization Of The Lyme Disease Spirochete From The Skin Of Patients With Erythema Chronicum Migrans", *J. Am. Acad. Dermatol.*, 13, pp. 444–449 (1985).

S. Bergström et al., "Molecular Analysis Of Linear Plasmid–Encoded Major Surface Proteins, OspA and OspB, Of The Lyme Disease Spirochete *Borrelia Burgdorferi*", *Mol. Micro.*, 3, pp. 479–486, (1989).

V.G. Bundoc and A.G. Barbour, "Clonal Polymorphisms Of Outer Membrane Protein OspB Of *Borrelia Burgdorferi*", *Infec. Immun.*, 57, pp. 2733–2741 (1989).

E. Fikrig et al., "Protection Of Mice Against The Lyme Disease Agent By Immunizing with Recombinant OspA", *Science*, 250, pp. 553–556 (1990).

(List continued on next page.)

*Primary Examiner*—Phuong T. Bui
(74) *Attorney, Agent, or Firm*—Fish & Neave; James F. Haley, Jr., Esq.; Jane T. Gunnison, Esq.

(57) ABSTRACT

Methods and compositions for the prevention and diagnosis of Lyme disease. OspA and OspB polypeptides and serotypic variants thereof, which elicit in a treated animal the formation of an immune response which is effective to treat or protect against Lyme disease as caused by infection with *B. burgdorferi*. Anti-OspA and anti-OspB antibodies that are effective to treat or protect against Lyme disease as caused by infection with *B. burgdorferi*. A screening method for the selection of those OspA and OspB polypeptides and anti-OspA and anti-OspB antibodies that are useful for the prevention and detection of Lyre disease. Diagnostic kits including OspA and OspB polypeptides or antibodies directed against such polypeptides.

86 Claims, 2 Drawing Sheets

OTHER PUBLICATIONS

G.S. Gassman et al., "Nucleotide Sequence Of A Gene Encoding The *Borrelia Burgdorferi* Flagelli", *Nuc. Acids Res.,* 17, p. 3590 (1989).

R.T. Greene et al., "Immunoblot Analysis Of Immunoglobulin G Response To The Lyme Disease Agent (*Borrelia Burgdorferi*) In Experimentally And Naturally Exposed Dogs", *J. Clin. Microbiol.,* 26, pp. 648–653 (1988).

T.R. Howe et al., "Organization Of Genes Encoding Two Outer Membrane Proteins Of The Lyme Disease Against *Borrelia Burgdorferi* Within A Single Transcriptional Unit", *Infect. Immun.,* 54, pp. 207–212 (1986).

W. Jiang et al., "Cross–Antigenicity Between The Major Surface Proteins (Osp–A and Osp–B) And Other Proteins Of *Borrelia–Burgdorferi*", *J. Immunol.,* 144, pp. 284–289 (1990).

R.C. Johnson et al., "Active Immunization Of Hamsters Against Experimental Infection With *Borrelia Burgdorferi*", *Infect. Immun.* 54, pp. 897–898 (1986).

R.C. Johnson et al., "Experimental Infection Of The Hamster With *Borrelia Burgdorferi*", *Ann. N.Y. Acad. Sci.,* 539, pp. 258–263 (1988).

R.C. Johnson et al., "Passive Immunization Of Hamsters Against Experimental Infection With The Lyme Disease Spirochete", *Infec. Immun.,* 53, pp. 713–714 (1986).

K.S. Kim et al., "Immunization Of Chickens With Live *Escherichia Coli* Expressing *Eimeria Acervulina* Merozoite Recombinant Antigen Induces Partial Protection Against Coccidiosis", *Infect. Immun.,* 57, pp. 2434–2440 (1989).

R.S. Lane and J.A Pascocello, "Antigenic Characteristics Of *Borrelia Burgdorferi* Isolates From Ixodid Ticks In California", *J. Clin. Microbiol.,* 27, pp. 2344–2349 (1989).

R.B. Lefebvre et al., "Characterization Of *Borrelia Burgdorferi* Isolates By Restriction Endonuclease Analysis And DNA Hybridization", *J. Clin. Microbiol.,* 27, pp. 636–639 (1989).

B.J. Luft et al., "Biochemical And Immunological Characterization Of The Surface Proteins Of *Borrelia Burgdorferi*", *Infec. Immun.,* 57, pp. 3637–3645 (1989).

D.C. Malloy et al., "Detection Of *Borrelia Burgdorferi* Using The Polymerase Chain Reaction", *J. Clin. Microbiol.,* 28, pp. 1089–1093 (1990).

D.R. Milich et al., "Antibody Production To The Nucleocapsid And Envelope Of The Hepatitis B Virus Primed By A Single Synthetic T Cell Site", *Nature,* 329, pp. 547–549 (1987).

D. Milich, "Synthetic T And B Cell Recognition Sites: Implications For Vaccine Development", *Adv. Immun.,* 45, pp. 195–282 (1989).

K.D. Moody et al., "Experimental Chronic Lyme Borreliosis In Lewis Rats", *Am. J. Trop. Med. Hyg.,* 42, pp. 165–174 (1990).

S.L. Neilsen et al., "Detection Of *Borrelia Burgdorferi* DNA By The Polymerase Chain Reaction", *Mol. Cell. Probes,* 4, pp. 73–79 (1990).

S.M.C. Newton, et al., "Immune Response To Cholera Toxin Epitope Inserted In Salmonella Flagellin", *Science,* 244, pp. 70–72 (1989).

J.E. Schaible et al., "The Severe Combined Immunodeficiency (SCID) Mouse: A Laboratory Model For The Analysis Of Lyme Arthritis And Carditis", *J. Exp. Med.,* 170, pp. 1427–1432 (1989).

U.E. Schaible et al., "A Mouse Model For *Borrelia Burgdorferi* Infection: Pathogenesis, Immune Response And Protection", *Behring Inst. Mitt.,* 88, pp. 59–67 (1991).

U.E. Schaible et al., "Demonstration of Antigen–Specific T Cells and Histopathological Alterations in Mice Experimentally Inoculated with *Borrelia burgdorferi*", *Infec. Immun.,* 57, pp. 41–47 (1989).

J.L. Schmitz et al., "Passive Immunization Prevents Induction of Lyme Arthritis In LSH Hamsters", *Infect. Immun.,* 58, pp. 144–148 (1990).

T.G. Schwan et al., "Changes In Infectivity And Plasmid Profile Of The Lyme Disease Spirochete, *Borrelia Burgdorferi,* As A Result Of In Vitro Cultivation", *Infect. Immun.,* 56, pp. 1831–1836 (1988).

M.M. Simon et al., "A Mouse Model For *Borrelia Burgdorferi* Infection: Approach To A Vaccine Against Lyme Disease", *Immun. Today,* 12, pp. 11–16 (1991).

W.J. Simpson et al., "Reactivity of Human Lyme Borreliosis Sera With A 39–Kilodalton Antigen Specific To *Borrelia Burgdorferi*", *J. Clin. Microbiol.,* 28, pp. 1329–1337 (1990).

R. Wallich et al., "Cloning And Sequencing Of The Gene Encoding The Outer Surface Protein A (OspA) Of A European *Borrelia Burgdorferi* Isolate", *Nuc. Acid Res.,* 17, p. 8864 (1989).

B. Wilske et al., "Immunochemical Analysis Of The Immune Response In Late Manifestations Of Lyme Borreliosis", *Zbl. Bakt. Hyg.,* 267, pp. 549–558 (1988).

B. Wilske et al., "Immunochemical And Immunological Analysis Of European *Borrelia Burgdorferi* Strains", *Zbl. Bakt. Hyg.,* 263, pp. 92–102 (1986).

B. Wilske et al., "Antigenic Variability of *Borrelia Burgdorferi,*" *Ann N.Y. Acad. Sci.,* 539, pp. 126–143 (1988).

S.W. Barthold et al., "An Animal Model For Lyme Arthritis", *Ann. N.Y. Acad. Sci.,* 539, pp. 264–273 (1988).

D.E. Yelton and M.D. Scharff, "Monoclonal Antibodies: A Powerful New Tool In Biology And Medicine", *Ann. Rev. Biochem.,* 50, pp. 657–680 (1981).

Aguila, H.L. et al., "Class and Subclass Switching of Hybridomas In Vitro," *Immunochemica,* 11, pp. 1–4 (1989).

Barthold, S.W. et al., "An Animal Model For Lyme Arthritis," *Ann. N.Y. Acad. Sci.,* 539, pp. 264–273 (1988).

Bissett, M.L. et al., "Characterization of *Borrelia burgdorferi* Strains Isolated From *Ixodes pacificus* ticks in California," *J. Clin. Microbiol.,* 25, pp. 2296–2301 (1987).

Bruggeman, M. et al., "Comparison of the Effector Functions of Human Immunoglobins Using A Matched Set of Chimeric Antibodies," *J. Exptl. Med.,* 166, pp. 1351–1361 (1987).

Burgess et al., "Possible Dissociation of the Heparin–binding Mitogenic Activities of Heparin–binding (Acidic Fibroblast) Growth Factor–1 from Its Receptor–binding Activities by Site–directed Mutagenesis of a Single Lysine Residue," *J. Cell Biol.,* 111, pp. 2129–2138 (1990).

Gillies et al., "Antigen Binding and Biological Activities of Engineered Mutant Chimeric Antibodies With Human Tumor Specificities," *Human Antibodies and Hybridomas,* 1, pp. 47–54 (1990).

Harlow, E. and D. Lane, *Antibodies: A Laboratory Manual,* Cold Spring Harbor Laboratory (1988), pp. 285 and 287.

Harris, W. J. and S. Emery, "Therapeutic Antibodies—The Coming of Age," *Trends in Biotechnology,* 10, pp. 42–44 (1993).

Houghten et al., "Relative Importance of Position and Individual Amino Acid Residues in Peptide Antigen–Antibody Interactions: Implications in the Mechanism of Antigenic Drift and Antigenic Shift," *Vaccines*, 86, pp. 21–25.

Kaufman, B.M. et al., "Monoclonal Antibodies Reactive With K1–Encapsulated *Escherichia coli* Lipopolysaccharide Are Opsonic and Protect Mice Against Lethal Challenge," *Inf. and Immun.*, 52, pp. 617–619 (1986).

Lazar et al., "Transforming Growth Factor α: Mutation of Aspartic Acid 47 and Leucine 48 Results in Different Biological Activities," *Molec. and Cellular Biol.*, 8, pp. 1247–1252 (1988).

McGrath et al., "Identification of an Immunologically Important Hypervariable Domain of Major Outer Surface Protein A," *Infect. and Immun.*, 63, pp. 1356–1361 (1995).

Olsson, I. et al., "IgG Subclasses of Specific Antibodies in *Ixodes ricinus*–borne Borreliosis," *Clin. Exp. Immunol.*, 69, pp. 618–623 (1987).

Osband, M.E. and S. Ross, "Problems in the Investigational Study and Clinical Use of Cancer Immunotherapy," *Immunol. Today*, 11, pp. 193–195 (1990).

Sadziene, A. et al., "In Vitro Inhibition of *Borrelia burgdorferi* Growth By Antibodies," *J. Infec. Dis.*, 167, pp. 165–172 (1993).

Tao et al., "Studies of A Glycosylated Chimeric Mouse–Human IgG," *J. Immunol.*, 143, pp. 2595–2601 (1989).

Waldmann, T.A. "Monoclonal Antibodies in Diagnosis and Therapy," *Science*, 252, pp. 1657–1662 (1991).

Dykhuizen, D., et al., "*Borrelia burgdorferi* is Clonal: Implications for Taxonomy and Vaccine Development," *Proc. Natl. Acad. Sci.*, 90, pp. 10163–10167 (1993).

Fikrig, E. et al., "*Borrelia burgdorferi* Strain 25015: Characterization of Outer Surface Protein A and Vaccination Against Infection," *J. Immunol.*, 148, pp. 2256–2260 (1992).

Bergstrom et al 3:479–86, 1989.*

Howe, T.R. et al, Inf & Immun, 54(1):207–212, 1986.*

Barthold, S.W. et al, Annals New York Academy Sci, 539:264–273, 1988.*

Philipp, M.T. et al, Inf & Immun, 61(7):3047–3059, 1993.*

Bissett, M.L. et al, J Clin Micro, 25(12):2296–2301, Dec. 1987.*

* cited by examiner

FIG. 1A

```
ATG AAA AAA TAT TTA TTG GGA ATA GGT CTA ATA TTA GCC TTA ATA GCA TGT AAG CAA AAT
Met Lys Lys Tyr Leu Leu Gly Ile Gly Leu Ile Leu Ala Leu Ile Ala Cys Lys Gln Asn
 1                          10                          20

GTT AGC AGC CTT GAC GAG AAA AAC AGC GTT TCA GTA GAT TTG CCT GGT GAA ATG AAC GTT
Val Ser Ser Leu Asp Glu Lys Asn Ser Val Ser Val Asp Leu Pro Gly Glu Met Asn Val
                            30                          40

CTT GTA AGC AAA GAA AAA AAC AAA GAC GGC AAG TAC GAT CTA ATT GCA ACA GTA GAC AAG
Leu Val Ser Lys Glu Lys Asn Lys Asp Gly Lys Tyr Asp Leu Ile Ala Thr Val Asp Lys
                            50                          60

CTT GAG CTT AAA GGA ACT TCT GAT AAA AAC AAT GGA TCT GAT CTT GAA GTA CTT GAA AAA
Leu Glu Leu Lys Gly Thr Ser Asp Lys Asn Asn Gly Ser Asp Leu Glu Val Leu Glu Lys
                            70                          80

GCT GAC GAA AGT AAA GTA AAA TTA ACA ATT TCT GAC GAT CTA GGT CAA ACC ACA CTT GAA
Ala Asp Lys Ser Lys Val Lys Leu Thr Ile Ser Asp Asp Leu Gly Gln Thr Thr Leu Glu
                            90                          100

GTT TTC AAA GAA GAT GGC AAA ACA CTA TCA AAA AAA GTA ACT TCC AAA GAC AAG TCA
Val Phe Lys Glu Asp Gly Lys Thr Leu Ser Lys Lys Val Thr Ser Lys Asp Lys Ser
                            110                         120

TCA ACA GAA GAA AAA TTC AAT GAA AAA GGT GAA GTA TCT GAA ATA ACA ATA ACA AGA GCA
Ser Thr Glu Glu Lys Phe Asn Glu Lys Gly Glu Val Ser Glu Ile Thr Ile Thr Arg Ala
                            130                         140

GAC GGA ACC AGA CTT GAA CTT ACA GAA TAC ACA GAA ATT AAA AGC GAT GGA TCT GGA AAA GCT AAA GAG
Asp Gly Thr Arg Leu Glu Leu Thr Glu Tyr Thr Glu Ile Lys Ser Asp Gly Ser Gly Lys Ala Lys Glu
                            150                         160

GTT TTA AAA GGC TAT GTT ACT GTT ACT CTT GAA GGA CTT TTA AGT CTT ACT GCT GAA AAA ACA TTG GTG GTT
Val Leu Lys Gly Tyr Val Thr Val Thr Leu Glu Gly Leu Thr Ala Glu Lys Thr Leu Val Val
                            170                         180

AAA GAA ACT GTT ACT TTA AGC AAT ATT TCA AAA TCT GGG GAA GTT TCA GTT GAA
Lys Glu Thr Val Thr Leu Ser Asn Ile Ser Lys Ser Gly Glu Val Ser Val Glu
```

FIG. 1B

```
                                                                        200
CTT AAT GAC ACT GAC AGT AGT GCT GCT AAA AAA ACT ACT TGG AAT TCA GGC ACT
Leu Asn Asp Thr Asp Ser Ser Ala Ala Lys Lys Thr Ala Ala Trp Asn Ser Gly Thr
    190                                               210                  220

TCA ACT TTA ACA ATT ACT GTA AAC AGT AAA ACT AAA GAC CTT GTG TTT ACA AAA GAA
Ser Thr Leu Thr Ile Thr Val Asn Ser Lys Thr Lys Asp Leu Val Phe Thr Lys Glu
                               230                                        240

AAC ACA ATT ACA GTA CAA CAA TAC GAC TCA AAT GGC ACC AAA TTA GAG GGG TCA GTT
Asn Thr Ile Thr Val Gln Gln Tyr Asp Ser Asn Gly Thr Lys Leu Glu Gly Ser Ala Val
                                   250                                    260

GAA ATT ACA AAA CTT GAT GAA ATT AAA AAC GCT TTA AAA
Glu Ile Thr Lys Leu Asp Glu Ile Lys Asn Ala Leu Lys
            270                   273
```

```
      EcoRI     rbs                    OspA                                          3'
5' AGAGAATTC AGGAGAATTTATGAAAAAATATTATT----------------------------

OspA                    BamHI             5'
3' ----------------------GAACTACTTAATTTTGCGAAATTT CCTAGGAGA
```

COMPOSITIONS AND METHODS FOR THE PREVENTION AND DIAGNOSIS OF LYME DISEASE

This is a division of U.S. application Ser. No. 08/320,161, filed Oct. 7, 1994, now U.S. Pat. No. 5,747,294, which is a continuation of U.S. application Ser. No. 07/682,355, filed Apr. 8, 1991, now abandoned, which is a continuation-in-part of U.S. application Ser. No. 07/602,551, filed Oct. 26, 1990, now abandoned, which is a continuation-in-part of U.S. application Ser. No. 07/538,969, filed Jun. 15, 1990, now abandoned. All are entitled "Compositions And Methods For The Prevention And Diagnosis Of Lyme Disease".

This invention was made with government support under Grant number AI 26815 awarded by the Department of Health and Human Services. The government has certain rights in the invention.

TECHNICAL FIELD OF THE INVENTION

This invention relates to compositions and methods useful for the prevention, treatment and diagnosis of Lyme disease in humans and other animals. More particularly, this invention relates to OspA and OspB polypeptides which are able to elicit in a treated patient, the formation of an immune response which is effective to treat or protect against Lyme disease. This invention also relates to a screening method for selecting the OspA and OspB polypeptides of this invention which are able to elicit such an immune response. Also within the scope of this invention are antibodies directed against the OspA and OspB polypeptides and diagnostic kits comprising the antibodies or the polypeptides.

BACKGROUND OF THE INVENTION

Lyme borreliosis is the most common vectorborne infection in the United States [S. W. Barthold, et al., "An Animal Model For Lyme Arthritis", *Ann. N.Y. Acad. Sci.*, 539, pp. 264–73 (1988)]. It has been reported in every continent except Antarctica. The clinical hallmark of Lyme Disease is an early expanding skin lesion known as *erythema migrans*, which may be followed weeks to months later by neurologic, cardiac, and joint abnormalities.

The causative agent of Lyme disease is a recently recognized spirochete known as *Borrelia burgdorferi*, transmitted primarily by ixodes ticks that are part of the *Ixodes ricinus* complex. *B. burgdorferi* has also been shown to be carried in other species of ticks and in mosquitoes and deer flies, but it appears that only ticks of the *I. ricinus* complex are able to transmit the disease to humans.

Lyme disease generally occurs in three stages. Stage one involves localized skin lesions (erythema migrans) from which the spirochete is cultured more readily than at any other time during infection [B. W. Berger et al., "Isolation And Characterization Of The Lyme Disease Spirochete From The Skin Of Patients With Erythema Chronicum Migrans", *J. Am. Acad. Dermatol.*, 3, pp. 444–49 (1985)]. Flu-like or meningitis-like symptoms are common at this time. Stage two occurs within days or weeks, and involves spread of the spirochete through the patient's blood or lymph to many different sites in the body including the brain and joints. Varied symptoms of this disseminated infection occur in the skin, nervous system, and musculoskeletal system, although they are typically intermittent. Stage three, or late infection, is defined as persistent infection, and can be severely disabling. Chronic arthritis, and syndromes of the central and peripheral nervous system appear during this stage, as a result of the ongoing infection and perhaps a resulting auto-immune disease [R. Martin et al., "*Borrelia burgdorferi*—Specific And Autoreactive T-Cell Lines From Cerebrospinal Fluid In Lyme Radiculomyelitis", *Ann Neurol.*, 24, pp. 509–16 (1988)].

*B. burgdorferi* is much easier to culture from the tick than from humans, therefore at present, Lyme disease is diagnosed primarily by serology. The enzyme-linked immunosorbent assay (ELISA) is one method of detection, using sonicated whole spirochetes as the antigen [J. E. Craft et al., "The Antibody Response In Lyme Disease: Evaluation Of Diagnostic Tests", *J. Infect. Dis.*, 149, pp. 789–95 (1984)]. However, serologic testing is not yet standardized, and results may vary between laboratories and commercial kits, causing false negative and, more commonly, false positive results. In addition, the disease often goes unrecognized, as the ticks are small and easy to miss, and the characteristic rash only occurs in 60–80% of cases and may be misinterpreted when it does occur.

At present, all stages of Lyme disease are treated with antibiotics. Treatment of early disease is usually effective, however the cardiac, arthritic, and nervous system disorders associated with the later stages often do not respond to therapy [A. C. Steere, "Lyme Disease", *New Eng. J. Med.*, 321, pp. 586–96 (1989).

Two lines of evidence suggest that the host immune response to specific antigens of *B. burgdorferi* may be partially responsible for the pathogenicity of Lyme disease. First, patients treated with corticosteroids (which suppress the immune system) show improvement of their symptoms [A. C. Steere et al., "Lyme Carditis: Cardiac Abnormalities Of Lyme Disease", *Ann. Intern. Med.*, 93, pp. 8–16 (1980)]. Second, some patients that do not respond to antibiotics appear to manifest an autoimmune disorder initiated by infection with *B. burgdorferi*.

Like *Treponema pallidum*, which causes syphilis, and leptospirae, which cause an infectious jaundice, Borrelia belong to the eubacterial phylum of spirochetes [A. G. Barbour and S. F. Hayes, "Biology Of Borrelia Species", *Microbiol. Rev.*, 50, pp. 381–400 (1986)]. *Borrelia burgdorferi* have a protoplasmic cylinder that is surrounded by a cell membrane, then by flagella, and then by an outer membrane. Embedded in the outer membrane are two major proteins, a 31 kd outer-surface protein A (OspA) [A. G. Barbour et al., "Lyme Disease Spirochetes And Ixodid Tick Spirochetes Share A Common Surface Antigenic Determinant Defined By A Monoclonal Antibody", *Infect. Immun.*, 41, pp. 795–804 (1983); J. L. Benach et al., "A Murine IgM Monoclonal Antibody Binds An Antigenic Determinant In Outer Surface Protein A, An Immunodominant Basic Protein Of The Lyme Disease Spirochete", *J. Immunol.*, 140, pp. 265–72 (1988)] and a 34 kd outer surface protein B (OspB) [A. G. Barbour et al., "Variation In A Major Surface Protein Of Lyme Disease Spirochetes", *Infect. Immun.*, 45, pp. 94–100 (1984)]. The two proteins have been shown to vary from different isolates or from different passages of the same isolate as determined by their molecular weights and reactivity with monoclonal antibodies. In addition, OspB may not be produced at all in culture [T. G. Schwan et al., "Changes In Infectivity And Plasmid Profile Of The Lyme Disease Spirochete, *Borrelia Burgdorferi*, As A Result Of In Vitro Cultivation", *Infect. Immun.*, 56, pp. 1831–36 (1988)].

Early in human infection, antibodies are generated primarily against a 41 kd flagella-associated antigen. Later on, high titer antibodies to both OspA and OspB appear [J. E. Craft et al., "Antigens Of *Borrelia Burgdorferi* Recognized During Lyme Disease: Appearance Of A New Immunoglobulin M Response And Expansion Of The Immunoglobulin G Response Late In The Illness", *J. Clin. Invest.*, 78, pp. 934–39 (1986)]. However, this humoral immune response is generally not sufficient to clear the system of the infective agent in experimentally infected laboratory rats. [K. D. Moody et al., "Experimental Chronic Lyme Borreliosis In Lewis Rats", *Am. J. Trop. Med. Hyg.* in press (1990)]. In addition, humans have been shown to be persistently infected for months or years. It has thus been suggested that the spirochete may be able to sequester itself in certain intracellular sites where it remains unavailable to circulating antibody molecules.

Development of a laboratory model for Lyme disease has proved elusive. Several groups have found spirochetemia in rabbits, Peromyscus mice, and Syrian hamsters after inoculation with *B. burgdorferi*, but no other manifestations of Lyme disease have been found. [W. Burgdorferi, "The New Zealand White Rabbit: An Experimental Host For Infecting Ticks With Lyme Disease Spirochetes", *Yale J. Biol. Med.*, 57, pp. 609–12 (1984); A. N. Kornblatt et al., "Experimental Lyme Disease In Rabbits: Spirochetes Found In Erythema Migrans And Blood", *Infect. Immun.*, 46, pp. 220–23 (1984); A. N. Kornblatt et al., "Infection In Rabbits With The Lyme Disease Spirochete", *Yale J. Biol. Med.*, 57, pp. 613–14 (1984); J. L. Benach et al., "Experimental Transmission Of The Lyme Disease Spirochete To Rabbits", *J. Infect. Dis.*, 150, pp. 786–87 (1984); J. G. Donahue et al., "Reservoir Competence Of White-Footed Mice For Lyme Disease Spirochetes", *Am. J. Trop. Med. Hyg.*, 36, pp. 92–96 (1987); E. C. Burgess et al., "Experimental Inoculation Of Peromyscus spp. With *Borrelia Burgdorferi*: Evidence Of Contact Transmission", *Am. J. Trop. Med. Hyg.*, 35, pp. 355–59 (1986); P. H. Duray and R. C. Johnson, "The Histopathology Of Experimentally Infected Hamsters With The Lyme Disease Spirochete, *Borrelia Burgdorferi*", *Proc. Soc. Exp. Biol. Med.*, 181, pp. 263–69 (1986); R. C. Johnson et al., "Infection Of Syrian Hamsters With Lyme Disease Spirochetes", *J. Clin. Microbiol.*, 20, pp. 1099–101 (1984).]

Several animal models have been developed however, which suggest that it may be possible to immunize against *B. burgdorferi* infection. Early studies with hamsters showed that passive immunization, i.e. transfer of serum from rabbits inoculated with *B. burgdorferi*, conferred protection from subsequent infection with the same strain [R. C. Johnson et al., "Passive Immunization Of Hamsters Against Experimental Infection With The Lyme Disease Spirochete", *Inf. Imm.*, 53, pp. 713–14 (1986)], however this immunity did not extend to strains from other geographic locations [R. C. Johnson et al. "Experimental Infection Of The Hamster With *Borrelia Burgdorferi*", *Ann. N.Y. Acad. Sci.*, 539, pp. 258–63 (1988)]. In addition, active immunization of hamsters with whole inactivated *B. burgdorferi* also confers immunity, but again it appears to be somewhat strain specific [R. C. Johnson et al., "Active Immunization Of Hamsters Against Experimental Infection With *Borrelia Burgdorferi*", *Inf. Imm.* 54, pp. 897–98 (1986)]. Hamsters are not an optimal model system however, as they do not appear to develop the clinical symptoms associated with Lyme disease.

An animal model utilizing laboratory rats demonstrated that although they become persistently infected and develop arthritis and carditis, these symptoms are inconsistent if the rats are infected at 3 weeks of age or older [S. W. Barthold et al., supra.]

Another animal model system using the severe combined immunodeficiency (SCID) mouse has also been developed. SCID mice infected with *B. burgdorferi* contract a chronic infection associated with arthritis and carditis, similar to Lyme disease in humans. [U. E. Schaible et al., "The Severe Combined Immunodeficiency Mouse: A Laboratory Model For The Analysis Of Lyme Arthritis And Carditis", *J. Exp. Med.*, 170, pp. 1427–32 (1989)]. Using this system, it was shown that *B. burgdorferi*-specific immune mouse sera as well as a monoclonal antibody to OspA, were able to prevent or slow the development of Lyme disease in SCID mice when passively transferred at the time of infection. [U. E. Schaible et al., "Monoclonal Antibodies Specific For The Outer Surface Protein A (OspA) Of *Borrelia Burgdorferi* Prevent Lyme Borreliosis In Severe Combined Immunodeficiency (SCID) Mice", *Proc. Natl. Acad. Sci. USA*, 87, pp. 3768–72 (1990)]. However, immunocompromised animals are not well suited for the study of potential vaccines. Others have attempted to infect immunocompetent strains of laboratory mice, but have failed, see S. W. Barthold et al., supra. Thus, additional animal systems and vaccine development is required.

As prevention of tick infestation is imperfect, and Lyme disease may be missed or misdiagnosed when it does appear, there exists an urgent need for the determination of the antigens of *B. burgdorferi* and related proteins which are able to elicit a protective immune response. In addition, in order to develop agents and methods to prevent and diagnose Lyme disease, an appropriate animal model which mimics the human disease is required with which to study and select such antigens, and to explore the immune response they may confer.

DISCLOSURE OF THE INVENTION

The present invention solves the problems referred to above by providing in one preferred embodiment OspA polypeptides and pharmaceutically effective compositions and methods comprising those polypeptides, which are useful for the treatment or prevention of Lyme disease. The preferred compositions and methods of this embodiment are characterized by OspA polypeptides which elicit in a treated patient, the formation of an immune response which is effective to treat or protect against Lyme disease as caused by infection with *B. burgdorferi*.

In another preferred embodiment, this invention provides OspB polypeptides and pharmaceutically effective compositions and methods comprising those polypeptides, which are useful for the treatment or prevention of Lyme disease. The preferred compositions and methods of this embodiment are characterized by OspB polypeptides which elicit in a treated patient, the formation of an immune response which is effective to treat or protect against Lyme disease as caused by infection with *B. burgdorferi*.

In yet another embodiment, this invention provides antibodies directed against the OspA or OspB polypeptides of this invention, and pharmaceutically effective compositions and methods comprising those antibodies. The antibodies of this embodiment are those that are immunologically reactive with the OspA or OspB polypeptides of this invention, and are effective to treat or protect against Lyme disease as caused by infection with *B. burgdorferi*.

This invention further provides a novel screening process, using a specific nonhuman, mammalian model, for selecting the preferred OspA and OspB polypeptides and antibodies of this invention that are effective to protect against Lyme disease. The screening process of this invention comprises the steps of:

1) immunizing a C3H/He mouse with an OspA or OspB polypeptide or antibody of this invention;

2) inoculating the immunized animal with *B. burgdorferi*; and 3) selecting those OspA or OspB polypeptides or antibodies which are effective to protect the animal against Lyme disease.

In another embodiment, this invention provides diagnostic means and methods characterized by OspA or OspB polypeptides, or antibodies directed against these polypeptides. These means and methods are useful for the detection of Lyme disease and *B. burgdorferi* infection. They are also useful in following the course of treatment against such infection.

Finally this invention provides DNA sequences that code for the OspA and OspB polypeptides of this invention, recombinant DNA molecules that are characterized by those DNA sequences, unicellular hosts transformed with those DNA sequences and molecules, and methods of using those sequences, molecules and hosts to produce the OspA and OspB polypeptides of this invention.

BRIEF DESCRIPTION OF THE DRAWING

FIG. 1 depicts the DNA and amino acid sequences of the OspA polypeptide of *B. burgdorferi* strain N40, and the sequence of the oligonucleotide primers used to amplify the gene.

DETAILED DESCRIPTION OF THE INVENTION

This invention relates to OspA and OspB polypeptides, anti-OspA and anti-OspB polypeptide antibodies, compositions containing the peptides and antibodies, and methods for the detection, treatment and prevention of Lyme disease. More specifically, in one embodiment, this invention relates to compositions and methods comprising OspA polypeptides that elicit in treated animals, including humans, an immune response which is sufficient to protect the animal for some period of time against Lyme disease-related disorders as a result of infection with *B. burgdorferi.*

In another embodiment, this invention relates to compositions and methods comprising OspB polypeptides that elicit in treated animals, including humans, an immune response which is sufficient to protect the animal for some period of time against Lyme disease-related disorders as a result of infection with *B. burgdorferi.*

In another embodiment, this invention relates to compositions and methods comprising anti-OspA or anti-OspB polypeptide antibodies that are effective to protect a treated animal for some period of time against Lyme disease-related disorders resulting from infection with *B. burgdorferi.*

In still another embodiment, this invention relates to diagnostic means and methods for the detection of Lyme disease.

In order to further define this invention, the following terms and definitions are herein provided.

As used herein, the "OspA polypeptides which confer protection against Lyme disease" are OspA polypeptides which prevent or lessen the severity, for some period of time, of any one of the disorders which result from infection with *B. burgdorferi*, including erythema migrans, arthritis, carditis, neurological disorders, and other Lyme disease-related disorders.

As used herein, "OspA polypeptide" denotes the OspA protein of SEQ ID NO: 4 and serotypic variants thereof, excluding strains ZS7 and B31; fragments containing at least 10 amino acids taken as a block from the amino acid sequence of the OspA protein of SEQ ID NO: 4 and serotypic variants thereof; and derivatives of either of the above, said derivatives being at least 80% identical in amino acid sequence to said OspA protein of SEQ ID NO: 4, serotypic variants thereof and fragments thereof. Alternatively, "OspA polypeptide" denotes polypeptides selected from the group consisting of: polypeptides that are immunologically reactive with antibodies generated by infection of a mammalian host with *B. burgdorferi*, which antibodies are immunologically reactive with the OspA protein of SEQ ID NO: 4 and serotypic variants thereof excluding ZS7 and B31 (i.e., excluding polypeptides that are immunologically reactive with antibodies that are immunologically reactive only with the OspA proteins of strains ZS7 and/or B31); polypeptides that are capable of eliciting antibodies that are immunologically reactive with *B. burgdorferi* and the OspA polypeptide of SEQ ID NO: 4 and serotypic variants thereof excluding ZS7 and B31, (i.e., excluding polypeptides that elicit antibodies that are immunologically reactive only with the OspA polypeptides of strains ZS7 and/or B31); and polypeptides that elicit in a treated mammalian host an immune response that is effective to protect against Lyme disease as caused by infection with *B. burgdorferi* and that are capable of eliciting antibodies that are immunologically reactive with the OspA polypeptide of SEQ ID NO: 4 and serotypic variants thereof.

As used herein, a "serotypic variant" of an OspA polypeptide, also referred to as an "OspA variant", is any polypeptide which may be encoded, in whole or in part, by a DNA sequence which hybridizes, at 20–27° C. below Tm, to any portion of the DNA sequence encoding the OspA polypeptide of SEQ ID NO: 4. Alternatively, a "serotypic variant" of an OspA polypeptide is any polypeptide which may be encoded, in whole or in part, by a DNA sequence which hybridizes to any portion of a DNA sequence encoding a derivative of the OspA protein of SEQ ID NO: 4 or fragments thereof, said derivatives being at least 80% identical in amino acid sequence to the OspA protein of SEQ ID NO: 4 or fragments thereof.

One of skill in the art will understand that serotypic variants of OspA polypeptides include those polypeptides encoded by DNA sequences of which any portion may be amplified by using the polymerase chain reaction and oligonucleotide primers derived from any portion of the DNA sequence encoding the OspA protein of SEQ ID NO: 4. In addition, serotypic variants of OspA polypeptides include those polypeptides encoded by DNA sequences of which any portion may be amplified by using the polymerase chain reaction and oligonucleotide primers derived from any portion of a DNA sequence encoding a derivative of the OspA protein of SEQ ID NO: 4 or fragments thereof, said derivatives being at least 80% identical in amino acid sequence to the sequence of the OspA protein of SEQ ID NO: 4 or fragments thereof.

According to one embodiment of this invention, a serotypic variant of an OspA polypeptide from *B. burgdorferi* strain N40 is provided. This variant (SEQ ID NO: 10), from strain 25015, differs in amino acid sequence from the OspA polypeptide of strain N40 at 39 positions. According to the definitions set forth above, the protein of SEQ ID NO: 10, fragments of at least 10 amino acids taken as a block from the amino acid sequence of SEQ ID NO: 10, or derivatives at least 80% identical in amino acid sequence to SEQ ID NO: 10 or fragments thereof, are all considered to be OspA polypeptides. In addition, polypeptides immunologically reactive with antibodies generated by infection of a mammalian host with *B. burgdorferi*, which antibodies are immunologically reactive with the protein of SEQ ID NO: 10 or fragments thereof, and polypeptides capable of eliciting antibodies that are immunologically reactive with *B. burgdorferi* and the protein of SEQ ID NO: 10, are also considered to be OspA polypeptides.

One of skill in the art will understand that probes and oligonucleotide primers derived from the DNA encoding the 25015 OspA variant (SEQ ID NO: 9), particularly from regions encoding amino acid substitutions as compared to the OspA polypeptide of strain N40 (SEQ ID NO: 4), may be used to isolate and clone further variants of surface proteins from other *B. burgdorferi* strains and perhaps from other spirochetes as well, which are useful in the methods and compositions of this invention.

As used herein, the "OspB polypeptides which confer protection against Lyme disease" are OspB polypeptides which prevent or lessen the severity, for some period of time, of any one of the disorders which results from infection with *B. burgdorferi*, including erythema migrans, arthritis, carditis, neurological disorders, and other Lyme disease related disorders.

As used herein, "OspB polypeptide" denotes: the OspB protein of *B. burgdorferi* strain B31 and serotypic variants thereof; fragments containing at least 10 amino acids taken as a block from the amino acid sequence of the OspB protein of *B. burgdorferi* strain B31 and serotypic variants thereof; and derivatives of either of the above, said derivatives being at least 80% identical in amino acid sequence to the OspB protein of *B. burgdorferi* strain B31, serotypic variants thereof and fragments thereof. Alternatively, "OspB polypeptide" denotes polypeptides selected from the group consisting of: polypeptides that are immunologically reactive with antibodies generated by infection of a mammalian host with *B. burgdorferi*, which antibodies are immunologically reactive with the OspB protein of *B. burgdorferi* strain B31 and serotypic variants thereof; polypeptides that are capable of eliciting antibodies that are immunologically reactive with *B. burgdorferi* and the OspB protein of *B. burgdorferi* strain B31 and serotypic variants thereof; and polypeptides that elicit in a treated mammalian host an immune response that is effective to protect against Lyme disease as caused by infection with *B. burgdorferi* and that are capable of eliciting antibodies that are immunologically reactive with the OspB protein of *B. burgdorferi* strain B31 and serotypic variants thereof.

As used herein, a "serotypic variant" of an OspB polypeptide is any polypeptide which may be encoded, in whole or in part, by a DNA sequence which hybridizes, at 20–27° below Tm, to any portion of the DNA sequence encoding the OspB polypeptide of SEQ ID NO: 11. Alternatively, a "serotypic variant" of an OspB polypeptide is any polypeptide which may be encoded, in whole or in part, by a DNA sequence which hybridizes to any portion of a DNA sequence encoding a derivative of the OspB protein of SEQ ID NO: 11 or fragments thereof, said derivatives being at least 80% identical in amino acid sequence to the OspB protein of SEQ ID NO: 11 or fragments thereof.

As with serotypic variants of OspA polypeptides, one of skill in the art will readily appreciate that serotypic variants of OspB polypeptides include those polypeptides encoded by DNA sequences of which any portion may be amplified by using the polymerase chain reaction and oligonucleotide primers derived from any portion of the DNA sequence encoding the OspB protein of SEQ ID NO: 11. In addition, serotypic variants of OspB polypeptides include those polypeptides encoded by DNA sequences of which any portion may be amplified by using oligonucleotide primers derived from any portion of a DNA sequence encoding a derivative of the OspB protein of SEQ ID NO: 11 or fragments thereof, said derivatives being at least 80% identical in amino acid sequence to the sequence of the OspB protein of SEQ ID NO: 11 or fragments thereof.

It should also be understood that each of the OspA and OspB polypeptides of this invention may be part of a larger protein. For example, an OspA polypeptide of this invention may be fused at its N-terminus or C-terminus to another OspA polypeptide, or to a non-OspA polypeptide or combinations thereof. OspA polypepticdes which may be useful for this purpose include polypeptides derived from SEQ ID NO: 4, SEQ ID NO: 10, and serotypic variants of either of the above. Non-OspA polypeptides which may be useful for this purpose include polypeptides derived from SEQ ID NO: 11 and serotypic variants thereof, the *B. burgdorferi* flagella-associated protein and fragments thereof, other *B. burgdorferi* proteins and fragments thereof, and non-*B. burgdorferi* proteins and fragments thereof.

In one embodiment of this invention, fusion proteins comprising multiple serotypic variants of OspA and/or OspB polypeptides are constructed for use in the methods and compositions of this invention. Such proteins are effective in the prevention, treatment and diagnosis of Lyme disease as caused by a wide spectrum of *B. burgdorferi* isolates.

The OspA and OspB polypeptides may also be part of larger multimeric proteins. These fusion proteins or multimeric proteins may be produced recombinantly, or may be synthesized chemically. They also may include OspA and OspB polypeptides fused or coupled to moieties other than amino acids, including lipids and carbohydrates.

As used herein, a "protective antibody" is an antibody that confers protection against Lyme disease as caused by infection with *B. burgdorferi*, when used to passively immunize a naive animal.

As used herein, a "protective epitopel" is (1) an epitope which is recognized by a protective antibody, and/or (2) an epitope which, when used to immunize an animal, elicits an immune response sufficient to prevent or lessen the severity for some period of time, of any one of the disorders which result from infection with *B. burgdorferi*. A protective epitope may comprise a T cell epitope, a B cell epitope, or combinations thereof.

As used herein, a "T cell epitope" is an epitope which, when presented to T cells by antigen presenting cells, results in a T cell response such as clonal expansion or expression of lymphokines or other immunostimulatory molecules. A T cell epitope may also be an epitope recognized by cytotoxic T cells that may affect intracellular *B. burgdorferi* infection. A strong T cell epitope is a T cell epitope which elicits a strong T cell response.

As used herein, a "B cell epitope" is the simplest spatial conformation of an antigen which reacts with a specific antibody.

As used herein, a "therapeutically effective amount of an OspA polypeptide" is the amount required to prevent or lessen the severity, for some period of time, of any one of the disorders which result from infection with *B. burgdorferi*.

As used herein, a "therapeutically effective amount of an OspB polypeptide" is the amount required to prevent or lessen the severity, for some period of time, of any one of the disorders which result from infection with *B. burgdorferi*.

As used herein, an "anti-OspA polypeptide antibody" is an immunoglobulin molecule, or portion thereof, that is immunologically reactive with an OspA polypeptide of the present invention.

As used herein, an "anti-OspB polypeptide antibody" is an immunoglobulin molecule, or portion thereof, that is immunologically reactive with an OspB polypeptide of the present invention.

An anti-OspA polypeptide antibody or anti-OspB polypeptide antibody may be an intact immunoglobulin molecule or a portion of an immunoglobulin molecule that contains an intact antigen binding site, including those portions known in the art as F(v), Fab, Fab' and F(ab')2. It should be understood that an anti-OspA polypeptide antibody or anti-OspB polypeptide antibody may also be a protective antibody.

As used herein, a "therapeutically effective amount of an ant:i-OspA polypeptide antibody" is the amount required to prevent or lessen the severity, for some period of time, of any one of the disorders which result from infection with B. burgdorferi.

As used herein, a "therapeutically effective amount of an anti-OspB polypeptide antibody" is the amount required to prevent or lessen the severity, for some period of time, of any one of the disorders which result from infection with B. burgdorferi.

The OspA polypeptides of this invention in addition to including polypeptides corresponding to the native polypeptides (e.g., SEQ ID NO: 4 and serotypic variants thereof) include fragments and derivatives of those polypeptides and fragments. The fragments of such native polypeptides contain at least 10 amino acids taken as a block from the sequence of the OspA polypeptide of SEQ ID NO: 4 and serotypic variants thereof. The derivatives of this invention are at least 80% identical in amino acid sequence to the OspA protein of SEQ ID NO: 4, serotypic variants thereof and fragments thereof.

Likewise, the OspB polypeptides of this invention in addition to including polypeptides corresponding to the native polypeptides (e.g., B31 OspB and serotypic variants thereof) include fragments and derivatives of those polypeptides and fragments. The fragments of such native polypeptides contain at least 10 amino acids taken as a block from the sequence of B31 OspB and serotypic variants thereof. The derivatives of this invention are at least 80% identical in amino acid sequence to the OspB protein of SEQ ID NO: 11, serotypic variants thereof and fragments thereof.

In accordance with the present invention, the preferred derivatives result when native OspA or OspB polypeptides or fragments are modified or subjected to treatments to enhance their immunogenic character in the intended recipient. For example, various amino acid substitutions, modifications or deletions may be carried out during or after preparation of the polypeptides. Such derivatives of native OspA and OspB polypeptides include, for example, derivatives which may be produced by reacting free amino, carboxyl, or hydroxyl side groups of the amino acid residues present in the polypeptide. They may also include polypeptides which result from substitution of one or more amino acids with a different natural amino acid, an amino acid derivative or non-native amino acid, conservative substitution being preferred. For example the following substitutions may be made: 3-methylhistidine may be substituted for histidine; 4-hydroxyproline may be substituted for proline; 5-hydroxylysine may be substituted for lysine; and the like.

The OspA and OspB polypeptides of the present invention may also be modified to increase their immunogenicity, for example by coupling to dinitrophenol groups or arsanilic acid, or by denaturation with heat and/or SDS. Particularly if the OspA and OspB polypeptides are small polypeptides synthesized chemically, it may be desirable to couple them to an immunogenic carrier. The coupling of course, must not interfere with the ability of either the polypeptide or the carrier to function appropriately. For a review of some general considerations in coupling strategies, see *Antibodies, A Laboratory Manual*, Cold Spring Harbor Laboratory, ed. E. Harlow and D. Lane (1988). Useful immunogenic carriers are well known in the art. Examples of such carriers are keyhole limpet hemocyanin (KLH); albumins such as bovine serum albumin (BSA) and ovalbumin, PPD (purified protein derivative of tuberculin); red blood cells; tetanus toxoid; cholera toxoid; agarose beads; activated carbon; or bentonite.

Any OspA or ospB polypeptide of the present invention may be used in the form of a pharmaceutically acceptable salt:. Suitable acids and bases which are capable of forming salts with the polypeptides of the present invention are well known to those of skill in the art, and include inorganic and organic acids and bases.

According to one embodiment of this invention, we describe a method which comprises the steps of treating a patient in a pharmaceutically acceptable manner with a therapeutically effective amount of an OspA polypeptide, or a fusion protein or a multimeric protein comprising an OspA polypeptide of this invention, which confers protection against Lyme disease in a manner sufficient to prevent or lessen the severity, for some period of time, of any one of the disorders which result from infection with B. burgdorferi. The OspA polypeptides that are preferred for use in such methods and compositions are those that contain protective epitopes. Such protective epitopes may be B cell epitopes, T cell epitopes, or combinations thereof.

According to another embodiment of this invention, we describe a method which comprises the steps of treating a patient in a pharmaceutically acceptable manner with a therapeutically effective amount of an OspB polypeptide, or a fusion protein or a multimeric protein comprising an OspB polypeptide of this invention, which confers protection against Lyme disease in a manner sufficient to prevent or lessen the severity, for some period of time, of any one of the disorders which result from infection with B. burgdorferi. The OspB polypeptides that are preferred for use in such methods and compositions are also those that contain protective epitopes, which may be B cell epitopes, T cell epitopes, or combinations thereof.

The most preferred OspA and OspB polypeptides of this invention for use in these compositions and methods are those containing both strong T cell and B cell epitopes. Without being bound by theory, we believe that this is the best way to stimulate high titer antibodies that are effective to neutralize B. burgdorferi infection. Such preferred OspA and OspB polypeptides will be internalized by B cells expressing surface immunoglobulin that recognizes the B cell epitope. The B cells will then process the antigen and present it to T cells. The T cells will recognize the T cell epitope and respond by proliferating and producing lymphokines which in turn cause B cells to differentiate into antibody producing plasma cells. Thus, in this system, a closed autocatalytic circuit exists which will result in the amplification of both B and T cell responses, leading ultimately to production of a strong immune response which includes high titer antibodies against the OspA or OspB polypeptide.

To prepare such preferred OspA and OspB polypeptides, in one embodiment, overlapping fragments of the OspA and OspB polypeptides of this invention are used. The polypeptides that contain B cell epitopes are identified by their ability to (1) be recognized by a protective anti-*B. burgdorferi* or anti-OspA or anti-OspB antibody (2) remove protective antibodies from polyclonal rabbit anti-*B. burgdorferi* serum or (3) elicit an immune response which is protective against Lyme disease as caused by infection with *B. burgdorferi*.

As recognition of T cell epitopes is MHC restricted, OspA and OspB polypeptides that contain T cell epitopes are identified in vitro by testing them for their ability to stimulate proliferation and/or cytokine production by T cell clones generated from humans of various HLA types, from the lymph nodes of C3H/He mice, or from domestic animals. Compositions comprising multiple T cell epitopes recognized by individuals with different Class II antigens are useful for prevention and treatment of Lyme disease in a broad spectrum of patients.

In this preferred embodiment of the present invention, an OspA or OspB polypeptide containing a B cell epitope is fused to one or more OspA or OspB polypeptides containing strong T cell epitopes. The fusion protein comprising the OspA or OspB polypeptide that carries both strong T cell and B cell epitopes is able to elicit high titer antibody responses effective to neutralize infection with *B. burgdorferi*.

Strong T cell and B cell epitopes have also been observed in components of other viruses. For example, strong T cell epitopes have been observed in hepatitis B virus core antigen (HBcAg). Furthermore, it has been shown that linkage of one of these segments to segments of the surface antigen of Hepatitis B virus, which are poorly recognized by T cells, results in a major amplification of the anti-HBV surface antigen response, [D. R. Milich et al., "Antibody Production To The Nucleocapsid And Envelope Of The Hepatitis B Virus Primed By A Single Synthetic T Cell Site", *Nature*, 329, pp. 547–49 (1987)]. Therefore, in et another preferred embodiment, OspA and OspB olypeptides containing B cell epitopes are fused to segments of HBcAG or to other antigens which contain strong T cell epitopes, to produce a fusion protein comprising an OspA or OspB polypeptide that can elicit a high titer antibody response. For instance, an OspA polypeptide containing a B cell epitope may be fused to a strong T cell epitope of the *B. burgdorferi* OspB or flagella-associated protein. Similarly, an OspB polypeptide containing a B cell epitope may be fused to a strong T cell epitope of the *B. burgdorferi* OspA or flagella-associated protein. Alternatively, an OspA or OspB polypeptide containing a T cell epitope may be fused to another *B. burgdorferi* protein or fragment thereof, containing a B cell epitope. Likewise a non-*B. burgdorferi* B cell epitope may be fused to a strong OspA or OspB T cell epitope of this invention, and so forth.

In a preferred embodiment of this invention, fusion proteins comprising OspA and/or OspB polypeptides are constructed comprising B cell and/or T cell epitopes from multiple serotypic variants of *B. burgdorferi*, each variant differing from another with respect to the locations or sequences of the epitopes within the OspA or OspB polypeptide. Such fusion proteins, when used in the methods and compositions of this invention, are particularly effective in the prevention, treatment and diagnosis of Lyme disease as caused by a wide spectrum of *B. burgdorferi* strains.

Multimeric proteins comprising an OspA or OspB polypeptide are also part of this invention. Preferably, they consist of multiple T or B cell epitopes or combinations thereof repeated within the same molecule, either randomly, or with spacers (amino acid or otherwise) between them. The preparation of multimeric proteins is well known in the art.

It will be readily appreciated by one of ordinary skill in the art that the OspA or OspB polypeptides of this invention, as well as fusions and multimeric proteins containing them, may be prepared by recombinant means, chemical means, or combinations thereof.

For example, OspA polypeptides may be generated by recombinant means using the OspA gene of *B. burgdorferi* strain N40 (SEQ ID NO: 3), or the DNA of SEQ ID NO: 9, or derivatives of either of the above. DNA encoding OspA and Ospb polypeptides and serotypic variants thereof and derivatives thereof may likewise be cloned, e.g., using PCR and oligonucleotide primers derived from the DNA sequence encoding the OspA and OspB polypeptides of *B. burgdorferi* strains N40 or 25015. Such DNA may be expressed to produce other OspA and OspB polypeptides which are useful in the methods and compositions of this invention. Oligonucleotide primers as well as conserved and divergent DNA sequences within the OspA and OspB genes may also be used to isolate and clone other related surface proteins from *B. burgdorferi* and related spirochetes which may contain regions of DNA sequence homologous to the OspA and OspB polypeptides of this invention.

If the OspA or OspB polypeptides of this invention are produced recombinantly they may be expressed in unicellular hosts. As is well known to one of skill in the art, in order to obtain high expression levels of foreign DNA sequences in a host, the sequences must be operatively linked to transcriptional and translational expression control sequences that are functional in the chosen expression host. Preferably, the expression control sequences, and the gene of interest, will be contained in an expression vector that further comprises a bacterial selection marker and origin of replication. If the expression host is a eukaryotic cell, the expression vector should further comprise an expression marker useful in the expression host.

The DNA sequences encoding the OspA and OspB polypeptides oE this invention may or may not encode a signal sequence. If the expression host is eukaryotic, it generally is preferred that a signal sequence be encoded so that the protein is secreted and matured from the eukaryotic host.

An amino terminal methionine may ox may not be present on the expressed OspA and OspB polypeptides of this invention. If the terminal methionine is not cleaved by the expression host, it may, if desired, be chemically removed by standard techniques.

A wide variety of expression host/vector combinations may be employed in expressing the DNA sequences of this invention. Useful expression vectors for eukaryotic: hosts, include, for example, vectors comprising expression control sequences from SV40, bovine papilloma virus, adenovirus, cytomegalovirus and retroviruses. Useful expression vectors for bacterial hosts include known bacterial plasmids, such as plasmids from *E. coli*, including col E1, pCR1, pBR322, pMB9 and their derivatives, wider host range plasmids, such as RP4, phage DNAs, e.g., the numerous derivatives of phage lambda, e.g., NM989, and other DNA phages. Useful expression vectors for yeast cells include the 2µ plasmid and derivatives thereof. Useful vectors for insect cells include pVL 941.

In addition, any of a wide variety of expression control sequences—sequences that control the expression of the DNA sequence when operatively linked to it—may be used in these vectors to express the DNA sequences of this invention. Such useful expression control sequences include the expression control sequences associated with structural genes of the foregoing expression vectors. Examples of useful expression control sequences include, for example, the early and late promoters of SV40 or adenovirus, the lac system, the trp system, the TAC or TRC system, the major operator and promoter regions of phage lambda, the control regions of fd coat protein, the promoter for 3-phosphoglycerate kinase or other glycolytic enzymes, the promoters of acid phosphatase, e.g., Pho5, the promoters of the yeast α-mating system and other sequences known to control the expression of genes of prokaryotic or eukaryotic cells or their viruses, and various combinations thereof.

In a preferred embodiment, OspA and OspB polypeptides are inserted into the expression vector pDC 197-12 and transcribed from the lambda $P_L$ promoter. Transcription in this system is controlled by the thermolabile repressor CI857.

In another preferred embodiment, DNA encoding OspA or OspB polypeptides of this invention is inserted in frame into an expression vector that allows high level expression of the polypeptide as a fusion protein. Such a fusion protein thus contains amino acids encoded by the vector sequences as well as amino acids of the OspA or OspB polypeptide. Expression of OspA and OspB polypeptides as fusion proteins may increase stability and/or facilitate purification.

A wide variety of unicellular host cells are useful in expressing the DNA sequences of this invention. These hosts may include well known eukaryotic and prokaryotic hosts, such as strains of *E. coli*, Pseudomonas, Bacillus, Streptomyces, fungi, yeast, insect cells such as *Spodontera frugiperda* (SF9), animal cells such as CHO and mouse cells, African green monkey cells such as COS 1, COS 7, BSC 1, BSC 40, and BMT 10, and human cells, as well as plant cells in tissue culture. We prefer *E. coli* A89 or JM109.

It should of course be understood that not all vectors and expression control sequences will function equally well to express the DNA sequences of this invention. Neither will all hosts function equally well with the same expression system. However, one of skill in the art may make a selection among these vectors, expression control sequences and hosts without undue experimentation and without departing from the scope of this invention. For example, in selecting a vector, the host must be considered because the vector must replicate in it. The vector's copy number, the ability to control that copy number, and the expression of any other proteins encoded by the vector, such as antibiotic markers, should also be considered.

In selecting an expression control sequence, a variety of factors should also be considered. These include, for example, the relative strength of the sequence, its controllability, and its compatibility with the DNA sequence of this invention, particularly as regards potential secondary structures. Unicellular hosts should be selected by consideration of their compatibility with the chosen vector, the toxicity of the product coded for by the DNA sequences of this invention, their secretion characteristics, their ability to fold the OspA or OspB polypeptide correctly, their fermentation or culture requirements, and the ease of purification from them of the products coded for by the DNA sequences of this invention.

Within these parameters, one of skill in the art may select various vector/expression control sequence/host combinations that will express the DNA sequences of this invention on fermentation or in large scale animal culture, e.g., CHO cells or COS 7 cells.

The molecules comprising the OspA and OspB polypeptides which are encoded by the DNA sequences of this invention may be isolated from the fermentation or cell culture and purified using any of a variety of conventional methods including: liquid chromatography such as normal or reversed phase, using HPLC, FPLC and the like; affinity chromatography (such as with inorganic ligands or monoclonal antibodies); size exclusion chromatography; immobilized metal chelate chromatography; gel electrophoresis; and the like. One of skill in the art may select the most appropriate isolation and purification techniques without departing from the scope of this invention.

In addition, the OspA and OspB polypeptides of this invention may be generated by any of several chemical techniques. For example, they may be prepared using the solid-phase synthetic technique originally described by R. B. Merrifield, "Solid Phase Peptide Synthesis. I. The Synthesis Of A Tetrapeptide", *J. Am. Chem. Soc.*, 83, pp. 2149–54 (1963), or they may be prepared by synthesis in solution. A summary of peptide synthesis techniques may be found in E. Gross & H. J. Meinhofer, 4 The Peptides: Analysis, Synthesis, Biology; Modern Techniques Of Peptide And Amino Acid Analysis, John Wiley & Sons, (1981) and M. Bodanszky, Principles Of Peptide Synthesis, Springer-Verlag (1984).

Typically, these synthetic methods comprise the sequential addition of one or more amino acid residues to a growing peptide chain. Often peptide coupling agents are used to facilitate this reaction. For a recitation of peptide coupling agents suitable for the uses described herein see M. Bodansky, supra. Normally, either the amino or carboxyl group of the first amino acid residue is protected by a suitable, selectively removable protecting group. A different protecting group is utilized for amino acids containing a reactive side group e.g. lysine. A variety of protecting groups known in the field of peptide synthesis and recognized by conventional abbreviations therein, may be found in T. Greene, Protective Groups In Organic Synthesis, Academic Press (1981).

According to another embodiment of this invention, anti-OspA polypeptide antibodies as well as anti-OspB polypeptide antibodies are generated. Such antibodies are immunoglobulin molecules or portions thereof that are immunologically reactive with an OspA or OspB polypeptide of the present invention. It should be understood that anti-OspA and anti-OspB polypeptide antibodies include antibodies immunologically reactive with fusion proteins and multimeric proteins comprising OspA or OspB polypeptides.

Anti-OspA and anti-OspB polypeptide antibodies of this invention may be generated by infection of a mammalian host with *B. burgdorferi*, or by immunization of a mammalian host with an OspA or OspB polypeptide of the present invention. Such antibodies may be polyclonal or monoclonal, it is preferred that: they are monoclonal. Methods to produce polyclonal and monoclonal antibodies are well known to those of skill in the art. For a review of such methods, see Antibodies, A Laboratory Manual, supra, and D. E. Yelton, et al., *Ann. Rev. of Biochem.*, 50, pp. 657–80 (1981). Determination of immunoreactivity with the OspA or OspB polypeptides of this invention may be made by any of several methods well known to those of skill in the art, including by immunoblot assay and ELISA.

Anti-OspA and anti-OspB polypeptide antibodies may be used in compositions and methods for the prevention and treatment of Lyme disease as caused by infection with *B. burgdorferi*. Anti-OspA and anti-OspB polypeptide antibodies may also be used to identify OspA and OspB polypeptides containing protective epitopes.

This invention also provides an animal model in which to screen the various OspA and OspB polypeptides and anti-OspA and anti-OspB polypeptide antibodies of this invention for their ability to confer protection against Lyme disease.

It will be understood that by following the screening process of this invention, described infra, one of skill in the art may determine without undue experimentation whether a particular OspA or OspB polypeptide or antibody would be useful in the prevention of Lyme disease. The screening process comprises the steps of 1) immunizing an animal with an OspA or ospB polypeptide or anti-OspA or anti-OspB polypeptide antibody;
2) inoculating the immunized animal with *B. burgdorferi*; and
3) selecting those OspA or OspB polypeptides or anti-OspA or anti-OspB polypeptide antibodies which confer protection against Lyme disease subsequent to inoculation with *B. burgdorferi*.

While any animal that is susceptible to infection with *B. burgdorferi* may be advantageously useful in this screening process, C3H/He mice are preferred, as they are not only susceptible to infection but are also susceptible to Lyme disease, as occurs in humans. Thus in C3H/He mice, the efficacy of responses to both infection and disease can be tested.

The immunization of the animal with the OspA or OspB polypeptide or anti-OspA or anti-OspB polypeptide antibody may be accomplished by standard procedures. For a detailed discussion of such techniques, see *Antibodies, A Laboratory Manual*, supra. Preferably, if a polypeptide is used, it will be administered with a pharmaceutically acceptable adjuvant, such as complete or incomplete Freund's adjuvant, RIBI (muramyl dipeptides) or ISCOM (immunostimulating complexes). Such adjuvants may protect the polypeptide from rapid dispersal by sequestering it in a local deposit, or they may contain substances that stimulate the host to secrete factors that are chemotactic for macrophages and other components of the immune system. Preferably the immunization schedule will involve two or more administrations of the OspA or OspB polypeptide, spread out over several weeks.

Once the OspA and OspB polypeptides or anti-OspA or anti-OspB polypeptide antibodies of this invention have been determined to be effective in the screening process of this invention, they may then be used in a therapeutically effective amount in pharmaceutical compositions and methods to treat or prevent Lyme disease which may occur naturally in humans and other animals.

The pharmaceutical compositions of this invention may be in a variety of conventional depot forms. These include, for example, solid, semi-solid and liquid dosage forms, such as tablets, pills, powders, liquid solutions or suspensions, liposomes, capsules, suppositories, injectable and infusible solutions. The preferred form depends upon the intended mode of administration and prophylactic application.

Such dosage forms may include pharmaceutically acceptable carriers and adjuvants which are known to those of skill in the art. These carriers and adjuvants include, for example, RIBI, ISCOM, ion exchangers, alumina, aluminum stearate, lecithin, serum proteins, such as human serum albumin, buffer substances, such as phosphates, glycine, sorbic acid, potassium sorbate, partial glyceride mixtures of saturated vegetable fatty acids, water, salts or electrolytes such as protamine sulfate, disodium hydrogen phosphate, sodium chloride, zinc salts, colloidal silica, magnesium trisilicate, polyvinyl pyrrolidone, cellulose-based substances, and polyethylene glycol. Adjuvants for topical or gel base forms may be selected from the group consisting of sodium carboxymethylcellulose, polyacrylates, polyoxyethylene-polyoxypropylene-block polymers, polyethylene glycol, and wood wax alcohols.

The vaccines and compositions of this invention may also include other components or be subject to other treatments during preparation to enhance their immunogenic character or to improve their tolerance in patients.

Generally, the OspA or OspB polypeptide may be formulated and administered to the patient using methods and compositions similar to those employed for other pharmaceutically important polypeptides (e.g., the vaccine against hepatitis).

Compositions comprising anti-OspA or anti-OspB polypeptide antibodies may be administered by a variety of dosage forms and regimens similar to those used for other passive immunotherapies and well known to those of skill in the art. In addition, it may be advantageous to couple such antibodies to toxins such as diphtheria, pseudomonas exotoxin, ricin A chain, gelonin, etc., or antibiotics such as penicillins, tetracyclines and chloramphenicol.

Any pharmaceutically acceptable dosage route, including parenteral, intravenous, intramuscular, intralesional or subcutaneous injection, may be used to administer the OspA or OspB polypeptide or anti-OspA or anti-OspB polypeptide antibody composition. For example, the polypeptide or antibody may be administered to the patient in any pharmaceutically acceptable dosage form including those which may be administered to a patient intravenously as bolus or by continued infusion over a period of hours, days, weeks or months, intramuscularly—including paravertebrally and periarticularly—subcutaneously, intracutaneously, intra-articularly, intrasynovially, intrathecally, intralesionally, periostally or by oral or topical routes. Preferably, the compositions of the invention are in the form of a unit dose and will usually be administered to the patient intramuscularly.

The OspA and OspB polypeptides or anti-OspA or anti-OspB polypeptide antibodies may be administered to the patient at one time or over a series of treatments. The most effective mode of administration and dosage regimen will depend upon the level of immunogenicity, the particular composition and/or adjuvant used for treatment, the severity and course of the expected infection, previous therapy, the patient's health status and response to immunization, and the judgment of the treating physician. For example, the more highly immunogenic the polypeptide, the lower the dosage and necessary number of immunizations. Similarly, the dosage and necessary treatment time will be lowered if the polypeptide is administered with an adjuvant. Generally the dosage will consist of 10 µg to 100 mg of the purified OspA or OspB polypeptide, and preferably, the dosage will consist of 100–1000 µg. Generally, the dosage for an anti-OspA or anti-OspB polypeptide antibody will be 0.5 mg–3.0 g.

In a preferred embodiment of this invention, the OspA or OspB polypeptide is administered with an adjuvant, in order to increase its immunogenicity. Useful adjuvants include RIBI, and ISCOM, simple metal salts such as aluminum hydroxide, and oil based adjuvants such as complete and incomplete Freund's adjuvant. When an oil based adjuvant is used, the OspA polypeptide usually is administered in an emulsion with the adjuvant.

In yet another preferred embodiment, *E. coli* expressing proteins comprising OspA and/or OspB polypeptides are administered orally to non-human animals to confer protection from infection and disease as caused by *B. burgdorferi*. For example, a palatable regimen of bacteria expressing an OspA and/or OspB polypeptide of this invention may be administered with animal food to be consumed by wild mice or deer, or by domestic animals. Ingestion of such bacteria may induce an immune response comprising both humoral and cell-mediated components. See J. C. Sadoff et al., "Oral *Salmonella Typhimurium* Vaccine Expressing Circumsporozoite Protein Protects Against Malaria", *Science*, 240, pp. 336–38 (1988) and K. S. Kim et al., "Immunization of Chickens With Live *Escherichia coli* Expressing *Eimeria acervulina* Merozoite Recombinant Antigen Induces Partial Protection Against Coccidiosis", *Inf. Immun.*, 57, pp. 2434–40 (1989).

According to yet another embodiment, anti-OspA and anti-OspB polypeptide antibodies as well as the OspA and OspB polypeptides of this invention, are useful as diagnostic agents for detecting infection with *B. burgdorferi*, because the polypeptides are capable of binding to antibody molecules produced in animals, including humans that are infected with *B. burgdorferi*, and the antibodies are capable of binding to *B. burgdorferi* or antigens thereof.

Such diagnostic agents may be included in a kit which may also comprise instructions for use and other appropriate reagents. The polypeptide or antibody may be labeled with a detection means that allows for the detection of the OspA or OspB polypeptide when it is bound to an antibody, or for the detection of the anti-OspA or anti-OspB polypeptide antibody when it is bound to *B. burgdorferi*.

The detection means may be a fluorescent labeling agent such as fluorescein isocyanate (FIC), fluorescein isothiocyanate (FITC), and the like, an enzyme, such as horseradish peroxidase (HRP), glucose oxidase or the like, a radioactive element such as $^{125}I$ or $^{51}Cr$ that produces gamma ray emissions, or a radioactive element that emits positrons which produce gamma rays upon encounters with electrons present in the test solution, such as $^{11}C$, $^{15}O$, or $^{13}N$.

The linking of the detection means is well known in the art. For instance, monoclonal anti-OspA or anti-OspB polypeptide antibody molecules produced by a hybridoma can be metabolically labeled by incorporation of radioisotope-containing amino acids in the culture medium, or polypeptides may be conjugated or coupled to a detection means through activated functional groups.

The diagnostic kits of the present invention may be used to detect the presence of a quantity of *B. burgdorferi* or anti-*B. burgdorferi* antibodies in a body fluid sample such as serum, plasma or urine. Thus, in preferred embodiments, an OspA or OspB polypeptide or anti-OspA or anti-OspB polypeptide antibody composition of the present invention is bound to a solid support typically by adsorption from an aqueous medium. Useful solid matrices are well known in the art, and include crosslinked dextran; agarose;

polystyrene; polyvinylchloride; cross-linked polyacrylamide; nitrocellulose or nylon-based materials; tubes, plates or the wells of microtiter plates. The polypeptides or antibodies of the present invention may be used as diagnostic agents in solution form or as a substantially dry powder, e.g., in lyophilized form.

OspA and OspB polypeptides and anti-OspA and anti-OspB polypeptide antibodies provide much more specific reagents than those currently available for diagnosis, and thus may alleviate such pitfalls as false positive and false negative results. One skilled in the art will realize that it may be advantageous in the preparation of such reagents to utilize OspA and OspB polypeptides comprising epitopes from other *B. burgdorferi* proteins, including the flagella-associated protein, and antibodies directed against such polypeptides.

The OspA and OspB polypeptides and anti-OspA and anti-OspB polypeptide antibodies of the present invention, and compositions and methods comprising them, may also be useful for detection, prevention, and treatment of other infections caused by spirochetes which may contain surface proteins sharing amino acid sequence or conformational similarities with the OspA or OspB polypeptides of the present invention. These other spirochetes include Borrelia Hermsii and Borrelia Recurientis, Leptospira, and Treponema.

In order that this invention may be better understood, the following examples are set forth. These examples are for purposes of illustration only, and are not to be construed as limiting the scope of the invention in any manner.

EXAMPLE I

Development of an Animal Model for Lyme Disease

We developed an animal model in which to screen the OspP, and OspB polypeptides and anti-OspA and anti-OspB polypeptide antibodies of the present invention for their ability to elicit an immune response effective to treat or protect against *B. burgdorferi* infection and/or Lyme disease, by testing numerous strains of inbred mice. We chose to use mice because of the extensive immunologic, biologic and genetic parameters available for manipulation.

We examined the susceptibility of various strains of mice to infection with the highly virulent N40 strain of *B. burgdorferi*, inoculated via several different routes. [S. W. Barthold et al., *J. Inf.Dis.*, 162, pp. 133–138 (1990).] We chose mice having maximum genetic disparity and representing different H-2 haplotypes. The mice used for these studies were Balb/cByJ, C3H/HeJ, C57BL/6J, SJL/J, and SWR/J mice, purchased from the Jackson Laboratory (Bar Harbor, Me.), and CRL/:SKH(hr/hr)Br (hairless) purchased from Charles River Laboratories (Raleigh, N.C.). All mice were housed in Micro-Isolator cages (Lab Products, Maywood, N.J.) and provided food (Agway, Syracuse, N.Y.) and water ad libidum.

First, we grew the N40 isolate of *B. burgdorferi* in modified Barbour-Stoenner-Kelly (BSK-II) medium [A. G. Barbour et al., *Yale Journal Of Biol. Med.*, 57, pp. 521–25 (1986)] at 34° C., to a concentration of approximately $1 \times 10^8$ viable (spiralling) organisms/ml, as determined by counting and on a hemacytometer using dark field microscopy.

We inoculated the various strains of mice with doses of spirochetes ranging from $1 \times 10^1$ to $1 \times 10^8$ at 3 days or 3 weeks of age, via intraperitoneal, intradermal, intragastric, and intranasal inoculations. After 30 days, the mice were sacrificed with carbon dioxide gas and exsanguinated by cardiocentesis.

We removed various organs from each mouse and cultured them for *B. burgdorferi* infection. Tissues were homogenized in 1 ml of BSK II medium, then a 0.5 ml aliquot of the homogenate was placed in 7 ml of BSK II medium and cultured for 2 weeks.

We evaluated brain, lung, liver, heart, spleen, kidney and joints of all four limbs (shoulder, elbow, carpus, metacarpus, hip knee, tarsus, metatarsus, and phalanges) from the infected mice for histopathology by immersion fixing these tissues in neutral-buffered formalin (pH 7.2). In addition, we demineralized the joints and processed and stained the tissues with hematoxylin-eosin by routine histological techniques.

We also tested the sera of infected mice for anti-*B. burgdorferi* antibody using an enzyme-linked immunosorbent assay (ELISA). In this assay, we used spirochetes as antigen, prepared as follows. We grew 650 ml of *B. burgdorferi* strain N40 in BSK II medium to a maximum density, by culturing at 33° C. for 2 weeks. We then pelleted the spirochetes at 12,000 rpm in a Beckman J4 centrifuge for 20 min. at 15° C. The pellet was washed twice with phosphate buffered saline (PBS), and finally resuspended in 10 ml PBS. The spirochetes were then sonicated at 15 second intervals for 3 min. on ice. We then centrifuged, as described supra and filtered the supernatant through a 0.45 micron filter. We determined the protein concentration of the filtrate by spectroscopy.

The ELISA was performed according to standard procedures using microtiter plates from Dynatech, Inc. coated with 0.1 ml of antigen at a concentration of 10 $\mu$g/ml, as described supra. The second antibody was labeled peroxidase goat anti-mouse IgG (Tago, Burlingame, Calif.)).

The results of these studies showed that C3H/He mice, upon intradermal infection with all doses ranging from $1 \times 10^1$–$1 \times 10^8$ *B. burgdorferi* strain N40, develop clinical symptoms of a disease that is remarkably similar to Lyme disease in humans. Mice inoculated intradermally at 3 weeks of age developed spirochetemia and severe arthritis within two weeks. A high proportion of infected mice also developed carditis. The results of the ELISA showed that C3H/He mice had high levels of anti-*B. burgdorferi* antibodies, and spirochetes were culturable from the spleens from day 3 to 5 after inoculation. C3H/He mice remained persistently infected for at least 12 months after inoculation, and had a 100% correlation between positive spirochetal spleen cultures, seroconversion, and disease. The results further indicated that arthritis and carditis occur at the same infection dose level, and seroconversion occurs only in mice that are actively infected. We therefore chose the C3H/He mouse as our animal model for Lyme disease in humans because it is a fully immunocompetent adult host that 1) is susceptible to *B. burgdorferi* infection with small numbers of organisms given intradermally, 2) develops multisystemic and persistent infection and 3) develops a 100% incidence of polyarthritis and carditis. These characteristics are unique to the C3H/He mouse and not available with other known animal models.

EXAMPLE II

Passive Immunization of C3H/He Mice

We produced polyclonal rabbit anti-*B. burgdorferi* N40 antiserum by inoculation of New Zealand white rabbits with $1 \times 10^8$ live *B. burgdorferi* intravenously at days 0, 14, 21, and 49. One week later, we bled the animals for serum. We then passively immunized C3H/He mice at 6 weeks of age with 0.1 ml of a 1:5 dilution of this polyclonal rabbit serum. The passively immunized mice and control mice immunized with normal rabbit serum were then challenged 17 hours later with $1 \times 10^4$ *B. burgdorferi* by intradermal inoculation as described supra. We sacrificed the mice after two weeks and analyzed their blood, spleens and joints as described supra.

We found that the control mice had developed spirochetemia and severe arthritis at their ankle joints, while in all of the passively immunized mice, arthritis was prevented and spirochetes could not be cultured from their blood or spleen. These studies demonstrated that rabbits infected with *B. burgdorferi* strain N40 produce antisera containing antibodies effective to neutralize *B. burgdorferi* infection in our in vivo infectivity assay.

We next determined if C3H/He mice could be passively immunized against Lyme disease by transfer of polyclonal anti-*B. burgdorferi* serum from infected C3H/He mice. We inoculated a group of healthy 3 week old C3H/He mice or New Zealand white rabbits subcutaneously with $1 \times 10^7$ killed *B. burgdorferi* strain N40 in complete Freund's adjuvant and boosted at 10 days with $1 \times 10^7$ killed *B. burgdorferi* strain N40 in incomplete Freund's adjuvant. We then collected serum from the immunized mice or rabbits and diluted it 1:5 with phosphate buffered saline (PBS).

We administered 0.1 ml of the serum intradermally to groups of five uninfected C3H/He mice. Control groups of mice were immunized with normal mouse or rabbit serum. One day after immunization, we inoculated the mice intradermally on the contralateral side with $1 \times 10^4$ *B. burgdorferi* strain N40 or strain B31. After 5 or 14 days, the mice were euthanized by exposure to carbon dioxide. We then removed approximately 95% of the spleen from each mouse, homogenized it, and placed approximately 50% of the homogenate in 7 ml of BSK II medium. We also removed blood by cardiac exsanguination and cultured 0.1 ml of the blood in 7 ml of BSK II medium. Both the spleen and blood cultures were then incubated at 33° C. for 2 weeks as described supra. We examined the cultures for the presence of spirochetes by dark field microscopy. Twenty high power fields were scanned. We also evaluated the histopathology of the heart and joints at 14 days after infection.

As shown in Table I, none of the passively immunized mice had positive spirochete cultures, while at least 1 to 100 spirochetes were detected in all of the control mice immunized with normal mouse or rabbit serum. Furthermore, the protective effect of the rabbit serum was maintained at a dilution of 1:500.

In addition to conferring protection from infection, the passive immunization also conferred protection from disease. These studies demonstrated that passive immunization is protective in the mouse model and this protection extends across strains. These studies also demonstrated that it is possible to generate, in C3H/He mice immunized with *B. burgdorferi*, an immune response which can be protective against Lyme disease in naive C3H/He mice.

TABLE I

|  | Blood cultures* | | Splenic cultures* | | Arthritis | Carditis |
| --- | --- | --- | --- | --- | --- | --- |
|  | 5 day | 14 day | 5 day | 14 day | 14 day | 14 day |
| Mice challenged with N40 Antiserum (Dilution) | | | | | | |
| Mouse anti-*B. burgdorferi* N40 (1:5) | 0/8 | | 0/8 | | | |
| Normal mouse serum (1:5) | 8/8 | | 8/8 | | | |
| Rabbit anti-*B. burgdorferi* N40 (1:5) | 0/10 | 0/10 | 0/5 | 0/10 | 0/10 | 0/10 |
| Rabbit anti-*B. burgdorferi* N40 (1:50) | 0/10 | | 0/5 | | | |
| Rabbit anti-*B. burgdorferi* | 0/10 | | 0/5 | | | |

TABLE I-continued

|  | Blood cultures* | | Splenic cultures* | | Ar-thri-tis | Car-di-tis |
| --- | --- | --- | --- | --- | --- | --- |
|  | 5 day | 14 day | 5 day | 14 day | 14 day | 14 day |
| N40 (1:500) Normal rabbit serum (1:5)** Mice challenged with B31 Antiserum (Dilution) | 9/10 | 8/10 | 8/10 | 6/9 | 10/10 | 10/10 |
| Rabbit anti-*B. burgdorferi* N40 (1:5) | | 0/5 | | 0/5 | 0/5 | 0/5 |
| Normal rabbit serum (1:5) | | 5/5 | | 4/5 | 5/5 | 5/5 |

*Expressed as number of positive cultures/total number of cultures.
**Either a blood or spleen culture was positive in all control animals.

EXAMPLE III

Cloning of the N40 OspA Gene

We cloned the OspA gene of *B. burgdorferi* strain N40 by the polymerase chain reaction [H. Erlich et al. Eds., "Polymerase Chain Reaction", Cold Spring Harbor Press, pp. 25–29 (1989)]. Spirochetes were grown in 10 ml BSK II medium at 34° C. for 7 days, then harvested by centrifugation at 16K in a Beckman J4 centrifuge for 30 minutes. Genomic DNA was purified by SDS lysis and phenol-chloroform extraction as described in F. Hyde and R. Johnson, "Genetic Relationship Of The Lyme Disease Spirochetes To Borrelia, Treponema, And Leotospira", spp. *J. Clin. Micro.*, 20, pp. 151–54 (1984).

We obtained a pair of oligonucleotides for use as primers in the amplification, from the oligonucleotide and protein synthesis center at Yale University. The sequence of the oligonucleotides was based on the known sequence of the OspA gene from *B. burgdorferi* strain B31 [S. Bergström, et al., "Molecular Analysis Of Linear Plasmid-Encoded Major Surface Proteins, OspA And OspB, Of The Lyme Disease Spirochaete *Borrelia Burgdorferi*", *Mol. Micro.*, 3, pp. 479–86 (1989)]. The first member of the pair corresponded to the first 17 nucleotides of the coding sequence of the B31 OspA gene, and included an EcoR1 site and ribosome binding site at the 5' end to facilitate cloning (SEQ ID NO: 1). The second member of the pair corresponded to the complement of the last nine amino acids of the B31 OspA gene, and included a BamH1 site, again to facilitate cloning (SEQ ID NO: 2). The sequence of these oligonucleotides is depicted in FIG. 1. We purified the oligonucleotides by desalting over a Sephadex G-25 column essentially as follows. The oligonucleotides were dissolved in 0.4 ml $dH_2O$ and 0.2 ml was then loaded onto a Sephadex G-25 column equilibrated with $H_2O$. Fractions of 200 µl, eluted from the column by adding 2.5 ml of $H_2O$, were assayed for DNA by spectrophotometry. The majority of the oligonucleotide eluted in the second fraction.

We then performed PCR in a 100 µl reaction containing 20 µM of each oligonucleotide primer, 10 µl of 1 ng/µl *B. burgdorferi* template DNA prepared as described supra, 0.5 µl Taq DNA polymerase (Cetus Perkin-Elmer), 16 µl of 1.25 mm dNTPs, 10 µl of 10×buffer (500 mM KCl, 100 mM Tris-Hcl pH 8.3, 15 mM $MgCl_2$) and $dH_2O$ to 100 µl. We initially denatured the template DNA at 94° C., and then performed 30 cycles of PCR using an annealing temperature of 40° C., and an extension temperature of 72° C.

The PCR amplified OspA gene was isolated from the genomic DNA by agarose gel electrophoresis on a 1% gel, and purified by electroelution onto a DEAE membrane (Schleicher & Schuell, Keene, N.H.). The purified DNA was eluted from the membrane by incubating the membrane in 500 µl 1M NaCl at 55° C. for 1 hr. The eluted DNA was then ethanol precipitated. We then partially digested the DNA with EcoR1 and BamH1 (to avoid cleavage at an expected internal EcoR1 site) and repurified the full length amplified gene by agarose gel electrophoresis and electroelution as described supra. The EcoR1-BamH1 fragment was then ligated using T4 DNA ligase (13oehringer Mannheim, Danbury, Conn.) into an EcoR1, BamH1 cleaved expression vector pDC 197-12 (Kindly provided by W. Fiers, University of Ghent) overnight at 15° C. The ligation mixture was phenol/chloroform extracted, ethanol precipitated and resuspended in 50 µl of $H_2O$.

We selected pDC 197-12 as the expression vector because it contains the bacteriophage lambda $P_L$ promoter and the thermolabile phage lambda cI857 repressor, which is able to completely suppress transcription from the lambda $P_L$ promoter. The cI857 repressor is active at 30° C., and inactive at 42° C., thus allowing inducible expression of genes controlled by the $P_L$ promoter. By growing bacteria containing pDC 197-12 at 30° C., large quantities of plasmid-containing bacteria can be obtained without concern for production of potentially toxic or growth inhibitory proteins. pDC 197-12 also contains a tetracycline resistance gene, allowing selection of positive transformants on agarose plates containing tetracycline.

We transformed the ligation mixture into competent *E. coli* strain A89 (Kindly provided by F. Goldberg, Harvard University) using electroporation, as follows. We first prepared competent A89 bacteria by culturing in 1 liter L-Broth to an $OD_{600}$ of 0.6. We then pelleted the cells at 4000 rpm for 15 minutes, resuspended in 0.5 liter cold $dH_2O$, pelleted and resuspended again in 0.5 liter cold $dH_2O$, pelleted and resuspended them in 10 ml 20% glycerol, and finally pelleted and resuspended in 2 ml of 10% glycerol. We then mixed 40 µl of competent cells in an electroporation cuvette with 5 µl of the ligated DNA. We electroporated the bacteria at 2.5 KV with an electroporator from BioRad (Richmond, Calif.) set at a capacitance of 25 microF and 200 ohms resistance. We then transferred the suspension to 1 ml of SOC broth [2 grams bactotryptone, 5 grams bactoyeast, 0.5 grams NaCl, and 20 mM glucose per liter], incubated with shaking for one hour at 37° C., and plated onto L-broth plates containing 15 µg/ml tetracycline.

EXAMPLE IV

Sequence Analysis of the OspA Gene from Strain N40

Colonies containing the 197-OspA-N40 plasmid were identified as follows. Colonies were picked into 2 ml L-Broth with tetracycline, and incubated with shaking overnight at 30° C. The cells were then pelleted, resuspended in 200 µl GTE buffer (50 mM glucose, 25 mM Tris, 10 mM EDTA) and incubated for 10 minutes at room temperature. We then added 400 µl of a solution containing 0.2N NaOH and 1.9% SDS and incubated again for 10 minutes. We then added 300 µl of 7.5 M ammonium acetate, and incubated for 10 minutes on ice. After spinning 10 min. at 12,000 rpm, we removed the supernatant and precipitated the DNA from it by adding 500 µl of isopropanol. The DNA was then completely digested with EcoR1 and BamH1 and electrophoresed on an agarose gel. The sequence of the OspA gene was determined using a Sequenase kit (U.S. Biochemical, Cleveland, Ohio) and oligonucleotide primers synthesized at Yale University.

As shown in FIG. 1, the OspA gene was found to be 819 nucleotides in length. By comparing the DNA sequence (SEQ ID NO: 3) of the N40 OspA gene to the sequence of the OspA gene of strain B31, we determined that N40 OspA differs from B31 OspA at 2 positions, corresponding to nucleotides 117 and 446. As a result of these differences, the OspA protein from N40 (SEQ ID NO: 4) has an asparagine at amino acid 39 instead of a lysine, and a glutamic acid at amino acid 149 instead of glycine. The sequence (SEQ ID NO: 3) of the N40 OspA gene was also compared to the sequence of the OspA gene from strain ZS7 [B. Wallich et al., "Cloning And Sequencing Of The Gene Encoding The Outer Surface Protein A (OspA) Of A European *Borrelia Burgdorferi* Isolate", *Nuc. Acid Res.*, 17, p. 8864 (1989)]. The N40 OspA sequence (SEQ ID NO: 3) differs from ZS7 at nucleotide 490, causing a glycine to occur at amino acid 164 instead of serine. These comparisons suggest that OspA is highly conserved among different *B. burgdorferi* isolates.

EXAMPLE V

Cloning of OspB and the 41 kd flagella-associated Protein

We cloned the genes for OspB and the flagella-associated protein from *B. burgdorferi* strain N40 using oligonucleotide primers and PCR, as described in Example III. The oligonucleotide primers used to amplify the OspB gene were (SEQ ID NO: 5) 5' AGAGAATTCAGGAGAATTTATGAGATTATTAATA 3' and (SEQ ID NO: 6) 3' GAAAGTCTCGAATTTTTGCTGAAATTTTCCTAGGTCT 5'. The sequence of these oligonucleotides is based on the known sequence of the OspB gene from *B. burgdorferi* strain B31 [S. Bergström, et al., supra]. The oligonucleotide primers used to amplify the 41 kd flagella associated protein were (SEQ ID NO: 7) 5' AGAGAATTCAGGAGATTTATGATTATCAATCATAA 3' and (SEQ ID NO: 8) 3' ACAAAACAGTAACGAATCTATTCCTAGGAGA 5'. The sequence of these oligonucleotides is based on the known sequence of the flagellin gene from *B. burgdorferi* strain B31 (G. S. Gassman, et al., "Nucleotide Sequence Of A Gene Encoding The *Borrelia Burgdorferi* flagellin," *Nuc. Acid Res.*, 17, pp. 3590 (1989)]. The amplified N40 OspB and 41 kd flagella-associated protein genes were then isolated and directionally cloned into pDC 197-12 as described supra.

EXAMPLE VI

Cloning of Additional *B. burgdorferi* Proteins

We clone additional genes from *B. burgdorferi* strain N40 by constructing an expression library in λZAP (Stratagene, San Diego, Calif.). To construct the library, we use 10 micrograms of genomic *B. burgdorferi* DNA, randomly sheared by repeated passage through a syringe, and methylated with EcoR1 methylase. We then ligate EcoR1 linkers onto the ends of the genomic DNA fragments, and insert them into the λZAP vector, which expresses DNA inserts at the EcoR1 site as lac fusion proteins. We induce the recombinant phage of the library to express the lac-*B. burgdorferi* fusion proteins by incubating the plaques on nitrocellulose filters soaked with IPTG, following the manufacturer's protocol. The fusion proteins bind to the filters, which are then screened by incubation with polyclonal anti-*B. burgdorferi* antiserum from C3H/He mice infected with *B. burgdorferi*, as described supra. We detect binding of the primary antibody by subsequent binding of alkaline phosphatase conjugated goat anti-mouse secondary antibody. The alkaline phosphatase which collects at the site of primary antibody binding will be detected by exposure to BCIP and NBT, using techniques well known in the art.

After identifying plaques expressing lac-*B. burgdorferi* fusion proteins, we excise the pBluescript plasmid from the λZAP phagemid particles by infecting with helper phage according to the manufacturer's instructions. As a result, we have several additional *B. burgdorferi* genes which encode proteins or fragments thereof, that are recognized by polyclonal anti-*B. burgdorferi* antiserum.

EXAMPLE VII

Expression of an OspA-derived Polypeptide N40-OspA

We induced the recombinant A89 bacteria harboring the OspA-197-N40 plasmid to express recombinant N40 OspA protein (N40-OspA) by culturing them in 3 ml BSK II medium overnight at 30° C., and then inducing at 42° C. for 2 hours. We then concentrated the cells to an $OD_{600}$ of 4.0, and boiled an aliquot of 100–500 μl of concentrated cells for 5 min. We then electrophoresed 50 μl of the boiled cells on an SDS-polyacrylamide gel and stained with Coomassie brilliant blue. A unique band was present in lanes of extracts from induced cultures, accounting for approximately 5% of the total bacterial protein. The unique band migrated at 31 kd, the size expected for the recombinant OspA protein.

In order to determine if the new band on the gel represented N40-OspA, we performed an immunoblot of the bacterial proteins as follows. We first induced the bacteria to express N40-OspA and electrophoresed boiled samples as described supra. We then transferred the proteins to nitrocellulose strips (Schleicher & Schuell, Keene, N.H.) by electrotransfer for 2.5 hrs. at 60 volts using an electrotransfer apparatus from BioRad. We then reacted the strips with a 1:100 dilution of anti-*B. burgdorferi* immune mouse serum, prepared as described supra, or with the anti-*B. burgdorferi* monoclonal antibody VIIIC3.78 prepared by fusion of spleen cells from mice immunized with whole, live *B. burgdorferi*, infra. The strips were incubated for 1 hour at room temperature, washed for 1 hour at room temperature with PBS, incubated with a 1:5200 dilution of alkaline phosphatase labeled goat anti-mouse IgG (TAGO) and developed with nitroblue tetrazolium 5-bromo 4-chloro-indolyl phosphate. The immunoblot showed that the unique 31 kd band expressed by the *E. coli* stained with mouse serum as well as the monoclonal antibody, positively identifying it as N40-OspA. By performing the experiment with osmotic shock extracts of the *E. coli* [H. C. Neu and L. A. Heppel, "The Release Of Enzymes From *Escherichia Coli* By Osmotic Shock During The Formation Of Spheroplasts", *J. Biol. Chem.*, 240, pp. 3685–3692 (1965)], we were able to determine that the recombinant N40-OspA protein is localized at least in part to the periplasmic space.

We also isolated the recombinant protein by transfer to an Immobilon membrane (Schleicher & Schuell, Keene, N.H.) and had the amino terminus sequenced at the Protein Chemistry Facility at Yale University. The sequence of the first 15 amino acids of the protein corresponded to the sequence predicted from the DNA sequence (SEQ ID NO: 3) of the N40 OspA gene, providing further evidence that N40-OspA was being expressed in the recombinant bacteria.

EXAMPLE VIII

Active Immunization of Mice with *E. coli* Expressing N40-OspA

We next determined if N40-OspA was able to elicit an immune response that was protective against Lyme disease.

We induced expression of the protein in a 3 ml culture of bacteria as described supra. We then pelleted the cells, resuspended them in 3 ml of PBS, pelleted them again, and resuspended in 1 ml of PBS. We then determined the number of cells by spectrophotometry at an $OD_{600}$, and diluted the cells to $5 \times 10^7$/ml in PBS.

We then injected groups of five C3H/He mice intraperitoneally with 1 ml of $5 \times 10^6$ live E. coli expressing N40-OspA, once per week for 3 weeks. As a control, we injected five mice with E. coli transformed with the vector, pDC197-12. We bled the mice on the fourth week and prepared an immunoblot, as described supra, to determine if the mice were synthesizing antibody against N40-OspA. In this blot we ran a protein extract of whole, heat killed B. burgdorferi strain N40, transferred the proteins to nitrocellulose strips and incubated the strips with a 1:100 dilution of serum from the actively immunized mice as described supra. By the fourth week after the initial injection, a strong immune response to N40-OspA was elicited in all of the actively immunized animals. The antibody response could be detected by immunoblot to a dilution of 1:1000.

During the fifth week, we challenged the mice with B. burgdorferi strain N40 to determine if active immunization would elicit a protective immune response against various strains of B. burgdorferi. Mice were infected intradermally with $1 \times 10^4$ B. burgdorferi strain N40, B31, or CD16, prepared as described supra. The mice were then sacrificed after 5 or 14 days, and evaluated for infection and disease as described supra.

As shown in Table II, the mice that were actively immunized with E. coli expressing N40-OspA were fully protected from infection with all strains of B. burgdorferi tested, as determined from blood and spleen cultures. In contrast, the control mice immunized with E. coli harboring the parent plasmid without the OspA gene, readily developed infection. Repeated experiments gave identical results. In addition, the majority of the immunized animals were protected from clinical disease at 14 days. (Chi square $p \leq 0.05$)

TABLE II

| Immunizing Agent | Borrelia strain | Blood cultures* 5 day | Blood cultures* 14 day | Splenic cultures* 5 day | Splenic cultures* 14 day | Arthritis 14 day | Carditis 14 day |
|---|---|---|---|---|---|---|---|
| E. coli expressing OspA | N40 | 0/10 | 0/5 | 0/10 | | 2/5 | 2/5 |
| | B31 | 0/5 | | 0/5 | | | |
| | CD16 | 0/5 | | 0/5 | | | |
| E. coli lacking OspA | N40 | 9/9 | 5/5 | 7/9 | | 5/5 | 5/5 |
| | B31 | 5/5 | | 5/5 | | | |
| | CD16 | 3/5 | | | | | |

*Expressed as number of positive cultures/total number of cultures.

EXAMPLE IX

Passive Immunization of Mice with Serum from Actively Immunized Mice

We next determined if passive immunization of mice with serum from mice actively immunized with E. coli expressing N40-OspA, was able to confer protection against infection with B. burgdorferi. We passively immunized mice as described supra, with 0.1 ml of serum from actively immunized mice, either undiluted or diluted 1:5. We used normal rabbit serum at a dilution of 1:5 as a control. The next day, we inoculated the mice with B. burgdorferi strain N40, and evaluated blood cultures 5 days after infection, as described supra.

As shown in Table III, the passively immunized mice were fully protected from infection at 5 ays suggesting that serum from mice actively immunized ith OspA is sufficient to confer protection from subsequent infection with B. burgdorferi.

TABLE III

| Passive Immunization | Blood Cultures* 5 day |
|---|---|
| E. coli expressing OspA (Undil.) | 0/4 |
| E. coli expressing OspA (1:5) | 0/4 |
| Normal rabbit serum (1:5) | 8/10 |

*Expressed as number of positive cultures/total number of cultures.

EXAMPLE X

Passive Immunization of Mice with anti-B. burgdorferi Monoclonal Antibodies

We prepared anti-B. burgdorferi monoclonal antibodies by fusion of spleen cells from mice infected with B. burgdorferi strain N40, to mouse P3X63Ag8 myeloma cells, according to methods well known to those of skill in the art. We then determined the isotypes of the monoclonals, and selected four for passive immunization: VIIIC3.78 (complement fixing IgG3); IG12.57 (non-complement fixing IgG1); IIIH2.33 (complement fixing IgG2a); and VIA12.71 (complement fixing IgG2a).

We immunized C3H/He mice with 0.1 ml of undiluted supernatant from monoclonal antibody producing cells, and the next day, inoculated the animals with B. burgdorferi strain N40, as described supra. Five days later, we tested blood samples for infection. As shown in Table IV, immunization with the complement fixing IgG3 monoclonal antibody VIIIC3.78 conferred full protection from infection, while immunization with the non-complement fixing IgG1 monoclonal did not confer protection. The two IgG2a monoclonals conferred intermediate protection, i.e., protection to some animals. These studies demonstrate that immunity to B. burgdorferi infection can be conferred by passive immunization with a monoclonal antibody. We deposited a hybridoma cell line producing the monoclonal antibody VIIIC3.78 on Oct. 25, 1990 under the rules and regulations of the Budapest Treaty, with In Vitro International, Inc., Linthicum, Md. This deposit was accorded accession number IVI 10256. The deposit was transferred to American Type Culture Collection, 12301 Parkiawn Drive, Rockville, Md., on Jun. 20, 1991, and given ATCC accession number HB 10878.

TABLE IV

| Monoclonal Antibody | Blood Cultures* 5 day |
|---|---|
| IgG3 - VIIIC3.78 | 0/5 |
| IgG1 - IG12.57 | 5/5 |
| IgG2a - IIIH2.33 | 1/5 |
| IgG2a - VIA12.71 | 2/4 |

*Expressed as number of positive cultures/total number of cultures.

EXAMPLE XI

Synthesis of OspA Fusion Proteins

We construct recombinant genes which will express fragments of N40-OspA in order to determine which fragments contain protective epitopes. First, we produce overlapping 200–300 bp fragments which encompass the entire nucleotide sequence of the N40 OspA gene, either by restriction enzyme digestion, or by amplification of specific sequences of 197-OspA-N40, using PCR and oligonucleotide primers containing restriction endonuclease recognition sequences, as described supra. We then directionally clone these fragments into pGEMEX (Promega, Madison Wis.) cleaved with EcoR1 and BamH1. pGEMEX allows high level expression of recombinant proteins as T7 gene 10 fusion proteins. Transcription of the T7-OspA fusion proteins is driven by the bacteriophage T7 promoter. The oligonucleotide primers used to direct the PCR are constructed so as to result in an amplified fragment which, when cloned into pGEMEX and expressed as a fusion protein, maintains the correct reading frame of the OspA protein. We express the OspA fragments as fusion proteins because small protein fragments are commonly not expressed stably in E. coli.

We transform E. coli JM 109 with recombinant pGEMEX plasmids by electroporation, as described supra. We use E. coli JM109 as the host, because it contains the gene for T7 RNA polymerase under the IPTG induced lac uv5 promoter. We induce the transformed bacteria with IPTG, and they produce T7 RNA polymerase, which directs up to 50% of the cell protein as recombinant T7-OspA fusion protein.

The T7-OspA fusion protein produced in this manner is insoluble, and can be easily purified by recovery of the insoluble pellet fraction, followed by solubilization of the recombinant protein in denaturants. We choose to use urea to solubilize the fusion protein from pGEMEX for purification.

Another way to synthesize fusion proteins is to utilize the vector pGEX-2T (Pharmacia, Piscataway, N.J.) which allows expression of inserted genes as glutathione S-transferase fusion proteins. We amplified the OspA gene from the N40 strain of B. burgdorferi as described supra, using oligonucleotide primers containing EcoR1 and BamH1 restriction sites. We then purified and cloned the PCR-amplified OspA gene into pGEX-2T in frame with the glutathione S-transferase gene, using methods well known to those of skill in the art. We then transformed E. coli strain JM109 using electroporation, and selected recombinants by plating on ampicillin-containing plates. We grew 500 ml cultures of the transformed bacteria, and induced production of the recombinant fusion protein, referred to as OspA 1–819, with 1 mM IPTG, according to the manufacturer's protocol. We then washed the cells in PBS, resuspended in 5 ml PBS with 1% Triton, and lysed the cells by sonication. we then centrifuged the lysate at 13K rpm for 10 minutes, and loaded the supernatant onto a glutathione sepharose 4B column (Pharmacia). We eluted OspA 1–819 with 5 mM glutathione, according to the manufacturer's instructions.

EXAMPLE XII

Active Immunization of Mice with OspA 1–819

We immunized mice with 20 micrograms of purified OspA 1–819 by subcutaneous injection, once per week for 3 weeks. As a control, we injected mice with purified glutathione S-transferase prepared as described in Example XI. We bled the mice on the fourth week and prepared an immunoblot as described in Example VII, to determine if the mice were synthesizing antibody against N40-OspA. We found that the mice immunized with OspA 1–819 produced a very strong immune response to N40-OspA, as an antibody response could be detected to a dilution of 1:64,000 by immunoblot.

We then challenged the mice with $1 \times 10^4$ B. burgdorferi strain N40 and evaluated them for infection and disease at 5 or 14 days, as described supra. As shown in Table V, histopathologic examination of the joints and heart showed no evidence of disease in animals immunized with OspA 1–819 and blood and spleen cultures showed no evidence of infection. In contrast, control animals readily developed infection as well as arthritis and carditis. These studies demonstrated that the immune response generated by immunization with purified OspA 1–819 is sufficient to fully protect against subsequent infection and the clinical manifestations of disease.

TABLE V

| Immunizing Agent | Blood Cultures* | | Splenic cultures* | Arthritis | Carditis |
|---|---|---|---|---|---|
| | 5 day | 14 day | 14 day | 14 day | 14 day |
| OspA 1-819 | 0/15 | 0/15 | 0/5 | 0/9 | 0/10 |
| Glutathione S-transferase | 6/12 | 5/5 | 3/5 | 10/10 | 10/10 |

*Expressed as number of positive cultures/total number of cultures.

EXAMPLE XIII

Identification of OspA Fragments that Elicit Protective Antibody Production—B Cell Evitopes One way to identify regions of the OspA protein that contain protective B-cell epitopes is to determine which regions of the OspA protein are recognized by monoclonal antibodies that confer protection against B. burgdorferi infection.

We began by producing fragments of the OspA protein. First, we PCR-amplified portions of the OspA gene using oligonucleotide primers containing EcoR1 and BamH1 sites as described supra. We synthesized fragments consisting of nucleotides 200–819 and 400–819 of SEQ ID NO: 3. We then cloned these fragments into pGEX-2T in frame with the glutathione S-transferase protein. We then transformed E. coli with the recombinant plasmids, and induced expression of the OspA fragments as glutathione S-transferase fusion proteins. We refer to those fusion proteins as OspA 200–819 and OspA 400–819.

Next, we prepared an immunoblot with whole cell extracts from E. coli expressing either the OspA fragment glutathione S-transferase fusion proteins, (OspA 200–819 and OspA 400–819) or the full length OspA-glutathionle S-transferase fusion protein (OspA 1–819). We then incubated the immunoblot with the monoclonal antibody VIIIC3.78, previously shown to confer protection against B. burgdorferi infection (see Example X). The monoclonal antibody reacted with all three fusion proteins.

These results suggest that the epitope recognized by the protective antibody VIIIC3.78 is encoded within a region of the OspA gene (SEQ ID NO: 3) between nucleotides 400–819. This example does not necessarily imply that the epitope recognized by VIIIC3.78 is the only protective epitope in the OspA protein. Nor does it imply that the region encoding the B-cell epitope recognized by VIIIC3.78 does not also contain a T-cell epitope. However, it does illustrate one method that may be used to identify protective epitopes of the OspA protein.

Another way to identify regions of OspA that contain B cell epitopes is to use OspA fusion proteins to absorb antibodies from protective polyclonal serum. The various T7-OspA or OspA-glutathione S-transferase fusion proteins are coupled to CnBr activated Sepharose in order to construct a column, using standard techniques.

We prepare polyclonal rabbit anti-*B. burgdorferi* antiserum as in Example II.

We then pass the rabbit serum over the OspA-fusion protein column, to absorb antibodies which recognize the fusion protein. The residual serum is then used to passively immunize C3H/He mice, as described supra.

After two days, the immunized mice are challenged with *B. burgdorferi* strain N40 and then sacrificed after two weeks as described supra. Joints are clinically and histologically examined for joint inflammation, and the spleen and blood are cultured for spirochetes. After two weeks, cultures are examined for spirochetes by dark field microscopy as described supra. We are able to determine which fusion proteins are able to elicit protective antibodies, because polyclonal rabbit serum containing antibodies which recognize such fusion proteins—containing B cell epitopes—will be depleted of the ability to confer protection to passively immunized mice.

Once we have localized various epitopes to regions of the fusion proteins, we conduct further analyses using short synthetic peptides of 5–35 amino acids. The use of synthetic peptides allows us to further define each epitope, while eliminating variables contributed by the non-OspA portion of the fusion protein.

EXAMPLE XIV

Immunization of C3H/He Mice with OspA 400–819

We immunized mice with 10 µg of either OspA 400–819 or OspA 1–819 in complete Freund's adjuvant, and boosted with another 10 µg in incomplete Freund's adjuvant twice at 10 day intervals. Fourteen days later, we challenged the mice with $1\times10^4$ *B. burgdorferi* strain N40, and evaluated for infection at 14 days. As shown in Table VI only 1 of the 5 mice immunized with OspA 400–819 showed evidence of infection, whereas all of the control mice had positive spirochete cultures. These results provide further evidence that the 400–819 fragment of SEQ ID NO:3 encodes an OspA polypeptide containing a protective epitope.

TABLE VI

| Immunizing Agent | Borrelia Strain | Blood Cultures* | Splenic Cultures* | Blood and/or Splenic Culture*** |
|---|---|---|---|---|
| N40-OspA 1-819** | N40 | 0/5 | 0/5 | 0/5 |
| OspA 400-819 | N40 | 1/5 | 0/5 | 1/5 |
| Glutathione S-transferase | N40 | 4/5 | 3/5 | 5/5 |

*Expressed as number positive cultures/total number of cultures
**Mice in this group had previously been immunized with OspA 1-819. They were last boosted approximately 3 months before initiation of this experiment.
***Expressed as number of mice with positive blood and/or splenic culture/total number of mice

EXAMPLE XV

Active Immunization of C3H/He Mice with OspA Fusion Proteins

OspA fusion proteins which are found to react with protective monoclonal antibodies or which deplete the polyclonal rabbit serum of protective antibodies, are used to actively immunize C3H/He mice. We use between 10 and 100 micrograms of the OspA fusion protein emulsified in equal volumes of Freund's adjuvant and boost twice at 2 and 4 weeks. After three weeks we bleed the animals and measure the indirect fluorescent antibody titer by means of Western blot.

We also immunize mice with *E. coli* expressing the recombinant OspA fusion protein, as described in Example VIII. The antibody responses elicited by both methods of immunization are compared for optimal production. We then infect the immunized mice at 14, 30 and 94 days following immunization, and sacrifice them 5, 14, or 60 days later. We evaluate the mouse joints for inflammation and culture the spleens and blood for spirochetes. We then compare the protective effect of the purified antigen and the *E. coli* expressing antigen.

EXAMPLE XVI

Identification of OspA Epitopes that Confer crossorotective Antibodies

Antibodies elicited in the actively immunized mice that are directed against epitopes that are shared among various strains of *B. burgdorferi*, will confer protection against infection with these various strains of *B. burgdorferi*. To determine which epitopes of N40-OspA are able to elicit such antibodies, we immunize C3H/He mice with the various OspA fusion proteins, and challenge the mice with various strains of *B. burgdorferi* as described supra. We have isolated over 200 *B. burgdorferi* specimens from New England. We inject these various specimens into C3H/He mice to determine which are infective and/or arthritogenic, and then inoculate the various infective strains into mice which have been actively immunized with OspA fusion proteins. we design a vaccine around the epitopes that are shown to confer protection against infection with many different strains of *B. burgdorferi*.

Tables VII and VIII show the results of experiments conducted to determine whether immunization with recombinant OspA would protect mice from infection with other strains of *B. burgdorferi*. We immunized mice either with 10 µg of OspA 1–819 or by i.p. injection of live *E. coli* expressing N40-OspA, as described supra. Mice were boosted twice, at 10 day intervals, with the same amount of antigen. Fourteen days after the second boost we inoculated the mice with $1\times10^4$ *B. burgdorferi* strain 297 (isolated from human spinal fluid). We then evaluated the mice for infection at 14 days, as described supra. Five of the mice were also evaluated for disease. As shown in Table VII, immunization with OspA from *B. burgdorferi* strain N40 conferred almost complete protection from infection, and complete protection from disease.

TABLE VII

| Immunizing Agent | Challenge | Sacrifice | Blood and/or Splenic Cultures* | Arthritis and/or Carditis |
|---|---|---|---|---|
| OspA 1-819 or *E. coli* expressing N40-OspA | 297 | 14d | 1/15 | 0/5 |
| Glutathione S-transferase or *E. coli* not expressing N40-OspA | 297 | 14d | 9/17 | 5/5 |

*Expressed as number of mice with positive blood and/or splenic culture/total number of mice evaluated Similar experiments were conducted with *B. burgdorferi* strain B31. In these experiments however, we also sought to determine the longevity of protection. Mice were immunized with 10 µg OspA 1–819 and boosted twice, as described sugra. We then infected the mice with *B. burgdorferi* strain B31 and evaluated for infection and disease at 6 months after challenge. As shown in Table VIII immunization with OspA 1–819 from *B. burgdorferi* strain N40 conferred complete and long-lasting protection from infection and disease as caused by *B. burgdorferi* strain B31.

TABLE VIII

| Immunizing Agent | Challenge | Sacrifice | Blood and/or Splenic Cultures* | Arthritis and/or Carditis |
|---|---|---|---|---|
| OspA 1-819 | B31 | 6 mo. | 0/6 | 0/6 |
| Glutathione S-transferase | B31 | 6 mo. | 4/6 | 6/6 |

*Expressed as number of mice with positive blood and/or splenic culture/total number of mice evaluated
**Disease at 6 months was evidenced by chronic scarring and plasma cell infiltrates indicative of resolving chronic infection.

EXAMPLE XVII

Identification of OspA Fusion Proteins Containing T cell Epitones

Stimulation in animals of a humoral immune response containing high titer neutralizing antibodies will-be facilitated by antigens containing both T cell and B cell epitopes. To identify those OspA fusion proteins containing T cell epitopes we infect C3H/He mice with *B. burgdorferi* strain N40 in complete Freund's adjuvant, as described supra. Ten days after priming, lymph nodes are harvested and in vitro T cell lines are generated. These T cell lines are then cloned using limiting dilution and soft agar techniques. We use these T cell clones to determine which OspA fusion proteins contain T cell epitopes. The T cell clones are stimulated with the OspA fusion proteins and syngeneic antigen presenting cells. Exposure of the T cell clones to fusion proteins that contain T cell epitopes causes the T cells to proliferate, which we measure by $^3$H-Thymidine incorporation. We also measure lymphokine production by the stimulated T cell clones by standard methods.

To determine T cell epitopes of OspA polypeptides recognized by human T cells, we isolate T cell clones from *B. burgdorferi*-infected patients of multiple HLA types. T cell epitopes are identified by stimulating the clones with various OspA fusion proteins, and measuring $^3$H-Thymidine incorporation. The various T cell epitopes are then correlated with Class II HLA antigens such as DR, DP, and DQ. The correlation is performed by utilization of B lymphoblastoid cell lines expressing various HLA genes.

When a given Tr cell clone is mixed with the appropriate B lymphoblastoid cell line and an OspA polypeptide, the B cell will be able to present the OspA polypeptide to the T cell. Proliferation is then measured by $^3$H-Thymidine incorporation.

We then synthesize a combination vaccine based on these multiple T cell epitopes. Such a vaccine is useful for treatment or prevention of Lyme disease in a broad spectrum of a given patient population.

We also identify stimulating T cell epitopes in other *B. burgdorferi* proteins such as OspB and the flagella-associated protein, and design combination vaccines based on these epitopes, in conjunction with B cell epitopes from OspA polypeptides.

EXAMPLE XVIII

Construction of OspA Fusion Proteins Comprising T and B cell Epitopes

After identifying the epitopes of N40-OspA that are recognized by T cells, we construct recombinant proteins comprising these epitopes as well as the B cell epitopes recognized by neutralizing antibodies, for example those in Example X. These fusion proteins, by virtue of containing both T cell and B cell epitopes, permit antigen presentation to T cells by B cells expressing surface immunoglobulin. These T cells in turn stimulate B cells that express surface immunoglobulin, leading to the production of high titer neutralizing antibodies.

We also construct OspA fusion proteins by linking regions of N40-OspA known to contain B cell epitopes to strong T cell epitopes of other antigens. We synthesize an oligonucleotide homologous to amino acids 120 to 140 of the Hepatitis B virus core antigen.

This region of the core antigen has been shown to contain a strong T cell epitope [D. R. Millich, et al., supra. The oligonucleotide is then ligated to the 5' and 3' ends of segments of DNA encoding the B cell epitopes recognized by neutralizing antibodies, as in Example X. The recombinant DNA molecules are then used to express a fusion protein comprising a B cell epitope from OspA and a T cell epitope from the core antigen, thus allowing production of a strong humoral immune response against. *B. burgdorferi*.

We also construct a plasmid containing the B cell epitopes of N40-OspA incorporated into the flagellin protein of Salmonella. Bacterial flagellin are potent stimulators of cellular and humoral responses, and can be used as vectors for protective antigens [S. M. C. Newton, C. Jacob, B. Stocker, "Immune Response To Cholera Toxin Epitope Inserted In Salmonella Flagellin", *Science*, 244, pp. 70–72 (1989)].

We cleave the cloned H 1-d flagellin gene of *Salmonella muenchens* at a unique Eco RV site in the hypervariable region. We then insert blunt ended fragments of the ospA gene encoding protective B cell epitopes using T4 DNA ligase. The recombinant plasmids are then used to transform non-flagellate strains of Salmonella for use as a vaccine. Mice are immunized with live and formalin killed bacteria and assayed for antibody production to protective antigen. In addition spleen cells are tested for proliferative cellular responses to the peptide of interest. Finally the mice immunized with this agent are challenged with *B. burgdorferi* as described supra.

We also construct OspA fusion proteins comprising B cell epitopes from OspA and T cell epitopes from OspB, the 41 kd flagella-associated protein, or other proteins isolated from the expression library constructed from *B. burgdorferi* DNA. We also construct OspA fusion proteins comprising T cell epitopes from OspA and B cell epitopes from OspB and/or the flagella-associated protein or other *B. burgdorferi* proteins. Construction of these fusion proteins is accomplished by recombinant DNA techniques well known to those of skill in the art. Fusion proteins and antibodies directed against them, are used in methods and compositions to detect, treat, and prevent Lyme disease as caused by infection with *B. burgdorferi*.

EXAMPLE XIX

Cloning and Sequence Analysis of a Serotypic Variant of the OspA Gene

B. burgdorferi strain 25015 was kindly provided by John Anderson. We isolated SEQ ID NO: 9, encoding a serotypic variant of an OspA polypeptide, using oligonucleotide primers (SEQ ID NO: 1 and SEQ ID NO: 2) and PCR amplification, as described in Example III. We then sequenced this gene using the Sequenase Kit, as described in Example IV.

As shown in SEQ ID NO: 9, the gene encoding this serotypic variant from strain 25015 was found to be 819 nucleotides in length. Like the OspA gene from strain N40, SEQ ID NO: 9 encodes a protein of 273 amino acids (SEQ ID NO: 10). However, the 25015 OspA variant migrates by SDS-PAGE at 32.5 kd rather than 31 kd. By comparing SEQ ID NO: 10 to the sequence of the N40 OspA protein (SEQ ID NO: 4), we determined that the 25015 OspA variant contains 39 amino acid substitutions compared to N40-OspA. These substitutions occur at positions 39, 47, 53, 55, 90, 95, 96, 102, 114, 133, 137, 138, 141, 144, 149, 161, 164, 176, 190, 198, 199, 207, 208, 214, 215, 217, 218, 229, 234, 240, 241, 245, 247, 251, 254, 258, 263, 264, and 273. The finding of an OspA variant that differs to such a large extent from other known OspA polypeptides was both surprising and promising. The OspA variant expressed by strain 25015 may represent a novel class of surface proteins, and/or the surface protein from a novel class of Borrelia.

EXAMPLE XX

Infection of Passively Immunized Mice with B. burgdorferi Strain 25015

We first determined whether passive immunization of C3H/He mice with serum from rabbits immunized with B. burgdorferi strain N40 could confer protection against subsequent infection with B. burgdorferi strain 25015. To produce polyclonal rabbit anti-B. burgdorferi N40 antiserum, we inoculated New Zealand white rabbits with 30 fg of extract from killed B. burgdorferi (approximately $1\times10^7$ spirochetes) in complete Freund's adjuvant, then boosted 2 weeks later with an additional 30 µg of extract in incomplete Freund's adjuvant. We used 0.1 ml of a 1:5 dilution of the rabbit serum to passively immunize five C3H/He mice, as described in Example II. Control mice were immunized with normal rabbit serum. After 17 hours we challenged the mice with $1\times10^4$ B. burgdorferi strain 25015. Two weeks later, we evaluated the mice for spirochetemia and disease. All of the immunized mice were positive for infection and disease, indicating that passive immunization with rabbit anti-B. burgdorferi strain 25015 serum does not confer protection from infection with strain 25015.

EXAMPLE XXI

Synthesis of 25015 Variant Glutathione S-transferase Fusion Protein

We inserted SEQ ID NO: 9, encoding the 25015 OspA variant, into the vector pGEX-2T using EcoR1 and BamH1 linkers as described in Example XI. We then expressed the variant as a glutathione S-transferase fusion protein, and purified the recombinant fusion protein on a glutathione sepharose 4B column, as described previously.

EXAMPLE XXII

Active Immunization of Mice with the 25015 Variant Fusion Protein

We immunized groups of 5 mice with 10 µg OspA 1–819 or 10 µg of the 25015 variant fusion protein and boosted twice at 10 day intervals, as described supra. Control mice were immunized with glutathione S-transferase. We then challenged the immunized mice 14 days later with $1\times10^4$ B. burgdorferi strain 25015, and evaluated for infection and disease after 20 days. As shown in Table IX preliminary results indicate that immunization with the 25015 variant conferred total protection from infection and substantial protection from disease, as caused by B. burgdorferi strain 25015.

TABLE IX

| Immunizing Agent | Borrelia strain | Blood cultures* | Splenic cultures* | Arthritis | Carditis |
|---|---|---|---|---|---|
| N40 OspA 1-819 | 25015 | 0/4 | 1/4 | 0/4 | 0/4 |
| 25015 variant fusion protein | 25015 | 0/3 | 0/3 | 0/3 | 1/3 |
| Glutathione S-transferase | 25015 | 2/5 | 2/5 | 1/5 | 1/5 |

*Expressed as number of positive cultures/total number of cultures

In the above experiment, immunization with OspA 1–819 from B. burgdorferi strain N40 also appeared to confer protection from infection and disease as caused by B. burgdorferi strain 25015. However, results of other experiments indicate that OspA from B. burgdorferi strain N40 is not able to confer effective protection against infection or disease as caused by B. burgdorferi strain 25015.

For example, we immunized 20 mice with OspA from B. burgdorferi strain N40, either by injection of recombinant fusion protein, or by i.p. inoculation of live E. coli expressing N40-OspA. Mice were boosted and then challenged 14 days later with $1\times10^4$ B. burgdorferi strain 25015, as described previously. Control mice were immunized with either glutathione S-transferase or E. coli transformed with the pDC 197-12 vector without insert. As shown in Table X, mice immunized with OspA from B. burgdorferi strain N40 were not effectively protected from infection with B. burgdorferi strain 25015.

TABLE X

| Immunizing Agent | Challenge | Blood and/or Splenic Cultures* | Carditis and/or Arthritis |
|---|---|---|---|
| OspA 1-819 or E. coli expressing N40-OspA | 25015 | 11/19 | 5/9 |
| Glutathione S-transferase or E. coli not expressing N40-OspA | 25015 | 18/20 | 7/10 |

*Expressed as number of mice with positive blood and/or splenic culture/ total number of mice evaluated Similarly, we immunized five mice with 10 µg of the 25015 variant fusion protein as described supra, and challenged with B. burgdorferi strain N40. Three of the five immunized mice had positive spirochete cultures at 14 days after infection. These results demonstrate that N40-OspA contains epitopes not shared by the 25015 variant, and similarly, the 25015 variant contains epitopes not shared by N40 OspA.

Identification of T and B cell epitopes within the 25015 variant and construction of fusion proteins containing these epitopes as well as epitopes from other ospA polypeptides and/or variants, will allow synthesis of vaccines that may confer protection against infection by a broad spectrum of B. burgdorferi isolates.

EXAMPLE XXIII

Construction of an OspA Polypeptide from N40-OspA and the 25015 Variant

We identify protective epitopes within 25015-OspA by producing overlapping fragments of the protein and testing each the for presence of T cell and B cell epitopes, and/or for the ability to confer protection against Lyme disease in our animal model system. We then select the fragments which encode both protective epitopes and amino acid substitutions compared to N40-OspA, and use these fragments to construct OspA fusion proteins comprising protective epitopes from strains N40 and 25015. Such fusion proteins confer protection against a broad range of *B. burgdorferi* isolates.

EXAMPLE XXIV

Sequence Analysis of the OspB Gene from Strain N40

We sequenced the OspB gene from *B. burgdorferi* strain N40 using the Sequenase Kit, as described in Example IV. The gene was found to be 888 nucleotides in length. We then compared the N40 OspB gene sequence to the sequence of the OspB gene from strain B31 (S. Bergström et al., supra), and determined that N40 OspB differs from B31 OspB at 9 positions corresponding to nucleotides 258, 376, 382, 385, 526, 577, 593, 729, and 758 (with nucleotides 1–3 corresponding to amino acid 1). The nucleotides found at those positions in OspB from strain N40 are, respectively: C, A, A, A, A, T, G, C, and C. As a result of the nucleotide substitution at position 577, the OspB mRNA from strain N40 has a stop codon (UAA) at the position corresponding to amino acid 176 instead of the Glu (GAA) found in B31-OspB. Expression of the N40 OspB gene in *E. coli* results in production of a protein which migrates at 24 kd, suggesting the protein is in fact truncated by 104 COOH-terminal amino acids when expressed in that system. We believe that *B. burgdorferi* strain N40 may be able to read through the stop codon. However, because *E. coli* produce a truncated N40-OspB protein, we chose to continue our studies using the OspB gene from *B. burgdorferi* strain B31. We next investigated the immune response to OspB using our animal model system and purified B31-OspB glutathione S-transferase fusion protein.

EXAMPLE XXV

Synthesis of B31-OspB Glutathione S-transferase Fusion Protein

We cloned the B31 OspB gene by PCR amplifying the OspB insert of plasmid pTRH46, kindly provided by A. G. Barbour. We then inserted the amplified OspB gene into the vector pGEX-2T, expressed the OspB protein as a glutathione S-transferase fusion protein, and purified the recombinant protein on a glutathione sepharose 4B column, as described in Example XI.

EXAMPLE XXVI

Active Immunization of Mice with Full-length OspB-glutathione S-transferase Fusion Protein We immunized mice with 10 μg of purified B31-OspB glutathione S-transferase fusion protein in complete Freund's adjuvant and boosted 3 times at 10 day intervals with 10 μg OspB fusion protein in incomplete Freund's adjuvant. Control mice were immunized with purified glutathione S-transferase. Mice immunized with the OspB fusion protein synthesized antibodies against B31-OspB which were detectable by immunoblot at a dilution of 1:15,000. We then challenged the mice 14 days after immunization with various doses of *B. burgdorferi* strain N40 or B31, and evaluated for infection and disease at 14 days.

As shown in Table XI, all of the control mice readily developed spirochetemia. In contrast, the majority of mice immunized with OspB were protected from infection. Animals inoculated with $1 \times 10^2$ or $1 \times 10^3$ spirochetes were also protected from disease, with the exception of one mouse that developed mild carditis. In contrast the same dosage of spirochetes caused disease in substantial numbers of the control mice.

TABLE XI

| Immunizing Agent | Borrelia strain (dose) | Cultures* | Arthritis and/or Carditis |
|---|---|---|---|
| B31-OspB Glutathione S-transferase | B31($10^4$) | 5/14 | 7/14 |
|  | B31($10^3$) | 0/5 | 0/5 |
|  | B31($10^2$) | 0/8 | 1/10 |
| Glutathione S-transferase | B31($10^4$) | 12/13 | 12/13 |
|  | B31($10^3$) | 2/5 | 4/5 |
|  | B31($10^2$) | 3/8 | 3/8 |
| B31-OspB Glutathione S-transferase | N40($10^4$) | 2/5 | 5/5 |
|  | N40($10^2$) | 0/5 |  |
| Glutathione S-transferase | N40($10^4$) | 5/5 | 5/5 |
|  | N40($10^2$) | 1/5 |  |

*Expressed as number of mice with positive blood and/or spleen cultures/total number of mice These initial studies demonstrate that the B31-OspB glutathione S-transferase fusion protein is capable of conferring partial protection from infection with *B. burgdorferi*, and full protection from infection and disease at lower doses of spirochetes. Therefore OspB, like OspA, contains protective epitopes.

Following the teachings of this invention, one of skill in the art can readily identify the protective epitopes within the OspB protein, and synthesize OspB polypeptides (including fusion proteins and multimeric proteins) that are able to confer full protection from Lyme disease as caused by infection with *B. burgdorferi*.

EXAMPLE XXVII

Oral Immunization of Mice with OspA

We cultured *E. coli* harboring the p197-OspA-N40 plasmid at 30° C. as described in Example VII. We induced expression of N40-OspA by raising the temperature to 42° C. for 2 hours, then harvested the bacteria by centrifugation and resuspended in PBS at a concentration of $1 \times 10^9$ bacteria/ml.

We used 0.1 ml of this suspension to orally inoculate C3H/He mice. Inoculation was performed by gavage using a ball tipped metal needle. We boosted the mice with the same amount of bacteria on days 10, 20, 30 and 40. Control mice were inoculated in a similar fashion with bacteria lacking the p197-OspA-N40 plasmid. We bled the mice 7 days after the second and fourth boosts and conducted immunoblots on extracts of *B. burgdorferi*, as described in Example VII. The sera obtained after the second boost was diluted 1:100. Sera obtained after the fourth (last) boost was diluted 1:100, 1:500, 1:1,000, 1:5,000 and 1:10,000.

Antibodies were detectable by immunoblot in sera obtained at both time points. The antibody titer obtained after the second boost was somewhat weaker than that obtained in animals immunized with a similar schedule of i.p. injections of 1×10⁶ $E.$ $coli$ expressing N40-OspA. However, the sera obtained after the fourth boost contained antibodies detectable at a dilution of 1:5000, indicating the mice had mounted a strong humoral immune response to N40-OspA by that time.

Fourteen days after the last boost, we challenged the mice by intradermal inoculation with 1×10⁴ $B.$ $burgdorferi$ strain N40 and evaluated for infection and disease at 5 or 14 days as described in Example II. As shown in Table XII, mice orally vaccinated with $E.$ $coli$ expressing N40-OspA were protected from infection and disease. In addition, the mice showed no evidence of bacteremia.

TABLE XII

| Oral Immunization | Sacrifice | Blood and/or Splenic Cultures* | Arthritis | Carditis |
|---|---|---|---|---|
| OspA | 5 days | 0/5 | | |
| Control | 5 days | 4/5 | | |
| OspA | 14 days | 0/5 | 0/5 | 0/5 |
| Control | 14 days | 3/4 | 5/5 | 5/5 |

*Expressed as number of mice with positive blood and/or splenic cultures/ total number mice These results demonstrate that oral vaccination with an OspA polypeptide is sufficient to protect mice from infection and disease as caused by $B.$ $burgdorferi$.

---

We claim:

1. An isolated polypeptide comprising at least 50 contiguous amino acids of SEQ ID NO: 10, wherein the polypeptide is immunogenic.

2. A fusion protein comprising a first polypeptide and an additional polypeptide, wherein said first polypeptide is a polypeptide according to claim 1.

3. A vaccine comprising a fusion protein according to claim 2.

4. A multimeric protein comprising a polypeptide according to claim 1.

5. A vaccine comprising a multimeric protein according to claim 4.

6. A vaccine comprising a polypeptide according to claim 1.

7. An isolated polypeptide selected from the group consisting of:
   (a) a polypeptide comprising the amino acid sequence set forth in SEQ ID NO: 10; and
   (b) a polypeptide comprising the amino acid sequence from position 2 to 273 of SEQ ID NO: 10.

8. The polypeptide according to claim 7, wherein the polypeptide contains one or more modifications selected from the group consisting of: reaction of free amino, carboxyl or hydroxyl side groups of the amino acid residues of the polypeptide, and reaction with acids or bases to form salts of the protein or polypeptide, wherein said polypeptide containing said modifications retains the immunogenicity of the unmodified polypeptide.

9. A diagnostic kit comprising instructions for use and a polypeptide according to any one of claims 7, 8 or 1.

10. A fusion protein comprising a first polypeptide and an additional polypeptide, wherein said first polypeptide is a polypeptide according to claim 8.

11. A vaccine comprising a fusion protein according to claim 10.

12. A multimeric protein comprising a polypeptide according to claim 8.

13. A vaccine comprising a multimeric protein according to claim 12.

14. A vaccine comprising a polypeptide according to claim 8.

15. A fusion protein comprising a first polypeptide and an additional polypeptide, wherein said first polypeptide is a polypeptide according to claim 7.

16. A diagnostic kit comprising instructions for use and a fusion protein according to any one of claims 15, 10 or 2.

17. A vaccine comprising a fusion protein according to claim 15.

18. The vaccine according to any one of claims 17, 11 or 3, wherein the fusion protein is crosslinked to an immunogenic carrier.

19. The vaccine according to claim 18, further comprising an adjuvant.

20. A method for treating or preventing B. burgdorferi infection and Lyme disease comprising the step of administering to a patient a vaccine according to claim 19.

21. A method for treating or preventing B. burgdorferi infection and Lyme disease comprising the step of administering to a patient a vaccine according to claim 18.

22. The vaccine according to any one of claims 17, 11 or 3, further comprising an adjuvant.

23. A method for treating or preventing B. burgdorferi infection and Lyme disease comprising the step of administering to a patient a vaccine according to claim 22.

24. A vaccine comprising a polypeptide according to claim 7.

25. The vaccine according to any one of claims 24, 14 or 6, wherein the polypeptide is crosslinked to an immunogenic carrier.

26. The vaccine according to claim 25, further comprising an adjuvant.

27. A method for treating or preventing B. burgdorferi infection and Lyme disease comprising the step of administering to a patient a multimeric protein according to claim 26.

28. A method for treating or preventing B. burgdorferi infection and Lyme disease comprising the step of administering to a patient a fusion protein according to claim 25.

29. The vaccine according to any one of claims 24, 14 or 6, further comprising an adjuvant.

30. A method for treating or preventing B. burgdorferi infection and Lyme disease comprising the step of administering to a patient a vaccine according to claim 29.

31. A multimeric protein comprising a polypeptide according to claim 7.

32. A diagnostic kit comprising instructions for use and a multimeric protein according to any one of claims 31, 12 or 4.

33. A vaccine comprising a multimeric protein according to claim 31.

34. The vaccine according to any one of claims 33, 13 or 5, wherein the multimeric protein is crosslinked to an imnmunogenic carrier.

35. The vaccine according to claim 34, further comprising an adjuvant.

36. A method for treating or preventing B. Burgdorferi infection and Lyme disease comprising the step of administering to a patient a vaccine according to claim 35.

37. A method for treating or preventing B. burgdorferi infection and Lyme disease comprising the step of administering to a patient a vaccine according to claim 34.

38. The vaccine according to any one of claims 33, 13 or 5, further comprising an adjuvant.

39. A method for treating or preventing B. burgdorferi infection and Lyme disease comprising the step of administering to a patient a vaccine according to claim 38.

40. A method for treating or preventing B. burgdorferi infection and Lyme disease comprising the step of administering to a patient a composition selected from the group consisting of:
   (a) a polypeptide according to any one of claims 7, 8 or 1;
   (b) a fusion protein according to any one of claims 15, 10 or 2;
   (c) a multimeric protein according to any one of claims 31, 12 or 4; and
   (d) a vaccine according to any one of claims 3, 5, 6, 11, 13, 14, 17, 24, or 33.

41. A method for detecting *B. burgdorferi* infection comprising the step of assaying a body fluid of a suspected infected mammalian host with a polypeptide according to any one of claims 7, 8 or 1, wherein said body fluid is contacted with said polypeptide and a complex comprising said polypeptide and an antibody in said body fluid is detected, said complex being indicative of *B. burgdorferi* infection.

42. A method for detecting *B. burgdorferi* infection comprising the step of assaying a body fluid of a suspected infected mammalian host with a fusion protein according to any one of claims 15, 10 or 2, wherein said body fluid is contacted with said fusion protein and a complex comprising said fusion protein and an antibody in said body fluid is detected, said complex being indicative of *B. burgdorferd* infection.

43. A method for detecting *B. burgdorferi* infection comprising the step of assaying a body fluid of a suspected infected mammalian host with a multimeric protein according to any one of claims 31, 12 or 4 wherein said body fluid is contacted with said multimeric protein and a complex comprising said multimeric protein and an antibody in said body fluid is detected, said complex being indicative of *B. burgdorferi* infection.

44. An isolated polypeptide comprising amino acids 149–164 of SEQ ID NO: 4, wherein the polypeptide is immunogenic.

45. A fusion protein comprising a first polypeptide and an additional polypeptide, wherein said first polypeptide is a polypeptide according to claim 44.

46. A vaccine comprising a fusion protein according to claim 45.

47. A multimeric protein comprising a polypeptide according to claim 44.

48. A vaccine comprising a multimeric protein according to claim 47.

49. A vaccine comprising a polypeptide according to claim 44.

50. An isolated polypeptide selected from the group consisting of:
   (a) a polypeptide comprising the amino acid sequence set forth in SEQ ID NO: 4;
   (b) a polypeptide comprising the amino acid sequence from position 2 to 273 of SEQ ID NO: 4;
   (c) a polypeptide comprising the amino acid sequence encoded by nucleotides 200–819 of SEQ ID NO: 3; and
   (d) a polypeptide comprising the amino acid sequence encoded by nucleotides 400–819 of SEQ ID NO: 3.

51. The isolated polypeptide according to claim 50, wherein the polypeptide contains one or more modifications selected from the group consisting of: reaction of free amino, carboxyl or hydroxyl side groups of the amino acid residues of polypeptide, and reaction with acids or bases to form salts of the protein or polypeptide, wherein the polypeptide containing the modifications retains the immunogenicity of the unmodified polypeptide.

52. A fusion protein comprising a first polypeptide and an additional polypeptide, wherein said first polypeptide is a polypeptide according to claim 51.

53. A vaccine comprising a fusion protein according to claim 52.

54. A multimeric protein comprising a polypeptide according to claim 51.

55. A vaccine comprising a multimeric protein according to claim 54.

56. A vaccine comprising a polypeptide according to claim 51.

57. A diagnostic kit comprising instructions for use and a polypeptide according to any one of claims 50, 51 or 44.

58. A fusion protein comprising a first polypeptide and an additional polypeptide, wherein said first polypeptide is a polypeptide according to claim 50.

59. A diagnostic kit comprising instructions for use and a fusion protein according to any one of claims 58, 53 or 46.

60. A vaccine comprising a fusion protein according to claim 58.

61. The vaccine according to claim 60, wherein the fusion protein is crosslinked to an immunogenic carrier.

62. A method for treating or preventing *B. burgdorferi* infection and Lyme disease comprising the step of administering to a patient a vaccine according to claim 61.

63. The vaccine according to claim 61, further comprising an adjuvant.

64. A method for treating or preventing *B. burgdorferi* infection and Lyme disease comprising the step of administering to a patient a vaccine according to claim 63.

65. The vaccine according to claim 60, further comprising an adjuvant.

66. A method for treating or preventing *B. burgdorferi* infection and Lyme disease comprising the step of administering to a patient a vaccine according to claim 65.

67. A multimeric protein comprising a polypeptide according to claim 50.

68. A diagnostic kit comprising instructions for use and a multimeric protein according to any one of claims 67, 55 or 48.

69. A vaccine comprising a multimeric protein according to claim 67.

70. The vaccine according to claim 69, wherein the multimeric protein is crosslinked to an immunogenic carrier.

71. A method for treating or preventing *B. burgdorferi* infection and Lyme disease comprising the step of administering to a patient a vaccine according to claim 70.

72. The vaccine according to claim 70, further comprising an adjuvant.

73. A method for treating or preventing *B. burgdorferi* infection and Lyme disease comprising the step of administering to a patient a vaccine according to claim 72.

74. The vaccine according to claim 69, further comprising an adjuvant.

75. A method for treating or preventing *B. burgdorferi* infection and Lyme disease comprising the step of administering to a patient a vaccine according to claim 74.

76. A vaccine comprising a polypeptide according to claim 50.

77. The vaccine according to claim 76, wherein the polypeptide is crossing to an immunogenic carrier.

78. The vaccine according to claim 77, further comprising an adjuvant.

79. A method for treating or preventing *B. burgdorferi* infection and Lyme disease comprising the step of administering to a patient a multimeric protein according to claim 78.

80. A method for treating or preventing *B. burgdorferi* infection and Lyme disease comprising the step of administering to a patient a fusion protein according to claim 77.

81. The vaccine according to claim 76, further comprising an adjuvant.

82. A method for treating or preventing *B. burgdorferi* infection and Lyme disease comprising the step of administering to a patient a vaccine according to claim 81.

83. A method for treating or preventing *B. burgdorferi* infection and Lyme disease comprising the step of administering to a patient a composition selected from the group consisting of:
   (a) a polypeptide according to any one of claims 50, 51 or 49;
   (b) a fusion protein according to any one of claims 58, 53 or 46;
   (c) a multimeric protein according to any one of claims 67, 55 or 48; and
   (d) a vaccine according to any one of claims 76, 60, or 69.

84. A method for detecting *B. burgdorferi* infection comprising the step of assaying a body fluid of a suspected infected mammalian host with a polypeptide according to any one of claims 50, 51 or 44, wherein said body fluid is contacted with said polypeptide and a complex comprising said polypeptide and an antibody in said body fluid is detected, said complex being indicative of *B. burgdorferi* infection.

85. A method for detecting *B. burgdorferi* infection comprising the step of assaying a body fluid of a suspected infected mammalian host with a fusion protein according to any one of claims 58, 53 or 46, wherein said body fluid is contacted with said fusion protein and a complex comprising said fusion protein and an antibody in said body fluid is detected, said complex being indicative of *B. burgdorferi* infection.

86. A method for detecting *B. burgdorferi* infection comprising the step of assaying a body fluid of a suspected infected mammalian host with a multimeric protein according to any one of claims 67, 55 or 48, wherein said body fluid is contacted with said multimeric protein and a complex comprising said multimeric protein and an antibody in said body fluid is detected, said complex being indicative of *B. burgdorferi* infection.

* * * * *

SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
      (A) LENGTH: 36 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (x) PUBLICATION INFORMATION:
      (A) AUTHORS: Bergstrom, S.
      (B) TITLE: Molecular Analysis Of Linear Plasmid-Encoded
          Major Surface Proteins, OspA And OspB, Of The Lyme
          Disease Spirochaete Borrelia Burgdorferi
      (C) JOURNAL: Mol. Microbiol.
      (D) VOLUME: 3
      (F) PAGES: 479-486
      (G) DATE: 1986

(xi) SEQUENCE DESCRIPTION: SEQ ID NO:1:

AGAGAATTCA GGAGAATTTA TGAAAAAATA TTTATT          36

(2) INFORMATION FOR SEQ ID NO:2:

(i) SEQUENCE CHARACTERISTICS:
      (A) LENGTH: 36 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (x) PUBLICATION INFORMATION:

(A) AUTHORS: Bergstrom, S.
(B) TITLE: Molecular Analysis Of Linear Plasmid-Encoded
    Major Surface Proteins, OspA And OspB, Of The Lyme
    Disease Spirochaete Borrelia Burgdorferi
(C) JOURNAL: Mol. Microbiol.
(D) VOLUME: 3
(F) PAGES: 479-486
(G) DATE: 1986

(xi) SEQUENCE DESCRIPTION: SEQ ID NO:2:

AGAGGATCCT TTTAAAGCGT TTTTAATTTC ATCAAG                                    36

(2) INFORMATION FOR SEQ ID NO:3:

(i) SEQUENCE CHARACTERISTICS:
        (A) LENGTH: 819 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (x) PUBLICATION INFORMATION:
        (A) AUTHORS: FIKRIG, EROL
            BARTHOLD, STEPHEN W.
            KANTOR, FRED S.
            FLAVELL, RICHARD A.
        (B) TITLE: PROTECTION OF MICE AGAINST THE LYME DISEASE
            AGENT BY IMMUNIZING WITH RECOMBINANT OspA
        (C) JOURNAL: Science
        (G) DATE: 26-OCT-1990

(xi) SEQUENCE DESCRIPTION: SEQ ID NO:3:

ATGAAAAAAT ATTTATTGGG AATAGGTCTA ATATTAGCCT TAATAGCATG TAAGCAAAAT          60

GTTAGCAGCC TTGACGAGAA AAACAGCGTT TCAGTAGATT TGCCTGGTGA AATGAACGTT         120

CTTGTAAGCA AAGAAAAAAA CAAAGACGGC AAGTACGATC TAATTGCAAC AGTAGACAAG         180

CTTGAGCTTA AAGGAACTTC TGATAAAAAC AATGGATCTG GAGTACTTGA AGGCGTAAAA         240

GCTGACAAAA GTAAAGTAAA ATTAACAATT TCTGACGATC TAGGTCAAAC CACACTTGAA         300

GTTTTCAAAG AAGATGGCAA AACACTAGTA TCAAAAAAAG TAACTTCCAA AGACAAGTCA         360

TCAACAGAAG AAAAATTCAA TGAAAAAGGT GAAGTATCTG AAAAAATAAT AACAAGAGCA         420

GACGGAACCA GACTTGAATA CACAGAAATT AAAAGCGATG GATCTGGAAA AGCTAAAGAG         480

GTTTTAAAAG GCTATGTTCT TGAAGGAACT TTAACTGCTG AAAAAACAAC ATTGGTGGTT         540

AAAGAAGGAA CTGTTACTTT AAGCAAAAAT ATTTCAAAAT CTGGGGAAGT TTCAGTTGAA         600

CTTAATGACA CTGACAGTAG TGCTGCTACT AAAAAAACTG CAGCTTGGAA TTCAGGCACT         660

TCAACTTTAA CAATTACTGT AAACAGTAAA AAAACTAAAG ACCTTGTGTT TACAAAAGAA         720

AACACAATTA CAGTACAACA ATACGACTCA AATGGCACCA AATTAGAGGG GTCAGCAGTT         780

GAAATTACAA AACTTGATGA AATTAAAAAC GCTTTAAAA                                819

(2) INFORMATION FOR SEQ ID NO:4:

(i) SEQUENCE CHARACTERISTICS:
        (A) LENGTH: 273 amino acids
        (B) TYPE: amino acid
        (C) STRANDEDNESS: single
        (D) TOPOLOGY: linear (ii) MOLECULE TYPE: protein -continued (iii) HYPOTHETICAL: NO (iv) ANTI-SENSE: NO (x) PUBLICATION INFORMATION:
    (A) AUTHORS: FIKRIG, EROL
        BARTHOLD, STEPHEN W.
        KANTOR, FRED S.
        FLAVELL, RICHARD A.
    (B) TITLE: PROTECTION OF MICE AGAINST THE LYME DISEASE
        AGENT BY IMMUNIZING WITH RECOMBINANT OspA
    (C) JOURNAL: Science
    (G) DATE: 26-OCT-1990

(xi) SEQUENCE DESCRIPTION: SEQ ID NO:4:

```
Met Lys Lys Tyr Leu Leu Gly Ile Gly Leu Ile Leu Ala Leu Ile Ala
1               5                   10                  15

Cys Lys Gln Asn Val Ser Ser Leu Asp Glu Lys Asn Ser Val Ser Val
            20                  25                  30

Asp Leu Pro Gly Glu Met Asn Val Leu Val Ser Lys Glu Lys Asn Lys
        35                  40                  45

Asp Gly Lys Tyr Asp Leu Ile Ala Thr Val Asp Lys Leu Glu Leu Lys
    50                  55                  60

Gly Thr Ser Asp Lys Asn Asn Gly Ser Gly Val Leu Glu Gly Val Lys
65                  70                  75                  80

Ala Asp Lys Ser Lys Val Lys Leu Thr Ile Ser Asp Asp Leu Gly Gln
                85                  90                  95

Thr Thr Leu Glu Val Phe Lys Glu Asp Gly Lys Thr Leu Val Ser Lys
                100                 105                 110

Lys Val Thr Ser Lys Asp Lys Ser Ser Thr Glu Glu Lys Phe Asn Glu
            115                 120                 125

Lys Gly Glu Val Ser Glu Lys Ile Ile Thr Arg Ala Asp Gly Thr Arg
        130                 135                 140

Leu Glu Tyr Thr Glu Ile Lys Ser Asp Gly Ser Gly Lys Ala Lys Glu
145                 150                 155                 160

Val Leu Lys Gly Tyr Val Leu Glu Gly Thr Leu Thr Ala Glu Lys Thr
                165                 170                 175

Thr Leu Val Val Lys Glu Gly Thr Val Thr Leu Ser Lys Asn Ile Ser
                180                 185                 190

Lys Ser Gly Glu Val Ser Val Glu Leu Asn Asp Thr Asp Ser Ser Ala
            195                 200                 205

Ala Thr Lys Lys Thr Ala Ala Trp Asn Ser Gly Thr Ser Thr Leu Thr
        210                 215                 220

Ile Thr Val Asn Ser Lys Lys Thr Lys Asp Leu Val Phe Thr Lys Glu
225                 230                 235                 240

Asn Thr Ile Thr Val Gln Gln Tyr Asp Ser Asn Gly Thr Lys Leu Glu
                245                 250                 255

Gly Ser Ala Val Glu Ile Thr Lys Leu Asp Glu Ile Lys Asn Ala Leu
            260                 265                 270

Lys
```

(2) INFORMATION FOR SEQ ID NO:5:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (x) PUBLICATION INFORMATION:
            (A) AUTHORS: Bergstrom, S.
            (B) TITLE: Molecular Analysis Of Linear Plasmid-Encoded
                Major Surface Proteins, OspA And OspB, Of The Lyme
                Disease Spirochaete Borrelia Burgdorferi
            (C) JOURNAL: Mol. Microbiol.
            (D) VOLUME: 3
            (F) PAGES: 479-486
            (G) DATE: 1986

(xi) SEQUENCE DESCRIPTION: SEQ ID NO:5:

AGAGAATTCA GGAGAATTTA TGAGATTATT AATA                                    34

(2) INFORMATION FOR SEQ ID NO:6:

(i) SEQUENCE CHARACTERISTICS:
            (A) LENGTH: 37 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (x) PUBLICATION INFORMATION:
            (A) AUTHORS: Bergstrom, S.
            (B) TITLE: Molecular Analysis Of Linear Plasmid-Encoded
                Major Surface Proteins, OspA And OspB, Of The Lyme
                Disease Spirochaete Borrelia Burgdorferi
            (C) JOURNAL: Mol. Microbiol.
            (D) VOLUME: 3
            (F) PAGES: 479-486
            (G) DATE: 1986

(xi) SEQUENCE DESCRIPTION: SEQ ID NO:6:

TCTGGATCCT TTTAAAGTCG TTTTTAAGCT CTGAAAG                                 37

(2) INFORMATION FOR SEQ ID NO:7:

(i) SEQUENCE CHARACTERISTICS:
            (A) LENGTH: 35 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (x) PUBLICATION INFORMATION:
            (A) AUTHORS: GASSMAN, G. S.
            (B) TITLE: NUCLEOTIDE SEQUENCE OF A GENE ENCODING THE
                BORRELIA BURGDORFERI FLAGELLIN
            (C) JOURNAL: Nucleic Acids Res.
            (D) VOLUME: 17
            (F) PAGES: 3590-3590
            (G) DATE: 1989

(xi) SEQUENCE DESCRIPTION: SEQ ID NO:7:

AGAGAATTCA GGAGATTTAT GATTATCAAT CATAA                                   35

(2) INFORMATION FOR SEQ ID NO:8:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (x) PUBLICATION INFORMATION:
        (A) AUTHORS: GASSMAN, G. S.
        (B) TITLE: NUCLEOTIDE SEQUENCE OF A GENE ENCODING THE
            BORRELIA BURGDORFERI FLAGELLIN
        (C) JOURNAL: Nucleic Acids Res.
        (D) VOLUME: 17
        (F) PAGES: 3590-3590
        (G) DATE: 1989

(xi) SEQUENCE DESCRIPTION: SEQ ID NO:8:

```
AGAGGATCCT TATCTAAGCA ATGACAAAAC A                              31
```

(2) INFORMATION FOR SEQ ID NO:9:

(i) SEQUENCE CHARACTERISTICS:
        (A) LENGTH: 819 base pairs
        (B) TYPE: nucleic acid
        (C) STRANDEDNESS: double
        (D) TOPOLOGY: linear (ix) FEATURE:
        (A) NAME/KEY: CDS
        (B) LOCATION: 1..819

(xi) SEQUENCE DESCRIPTION: SEQ ID NO:9:

```
ATG AAA AAA TAT TTA TTG GGA ATA GGT CTA ATA TTA GCT TTA ATA GCA      48
Met Lys Lys Tyr Leu Leu Gly Ile Gly Leu Ile Leu Ala Leu Ile Ala
 1               5                  10                  15

TGT AAG CAA AAT GTT AGC AGC CTT GAC GAG AAA AAC AGC GTT TCA GTA      96
Cys Lys Gln Asn Val Ser Ser Leu Asp Glu Lys Asn Ser Val Ser Val
                20                  25                  30

GAT TTG CCT GGT GAA ATG AAA GTT CTT GTA AGC AAA GAA AAA GAC AAA     144
Asp Leu Pro Gly Glu Met Lys Val Leu Val Ser Lys Glu Lys Asp Lys
         35                  40                  45

GAC GGC AAG TAC AGT CTA ATG GCA ACA GTA GAC AAG CTT GAG CTT AAA     192
Asp Gly Lys Tyr Ser Leu Met Ala Thr Val Asp Lys Leu Glu Leu Lys
     50                  55                  60

GGA ACA TCT GAT AAA AAC AAT GGA TCT GGG GTG CTT GAA GGC GTA AAA     240
Gly Thr Ser Asp Lys Asn Asn Gly Ser Gly Val Leu Glu Gly Val Lys
 65                  70                  75                  80

GCT GAC AAA AGC AAA GTA AAA TTA ACA GTT TCT GAC GAT CTA AGC ACA     288
Ala Asp Lys Ser Lys Val Lys Leu Thr Val Ser Asp Asp Leu Ser Thr
                 85                  90                  95

ACC ACA CTT GAA GTT TTA AAA GAA GAT GGC AAA ACA TTA GTG TCA AAA     336
Thr Thr Leu Glu Val Leu Lys Glu Asp Gly Lys Thr Leu Val Ser Lys
                100                 105                 110

AAA AGA ACT TCT AAA GAT AAG TCA TCA ACA GAA GAA AAG TTC AAT GAA     384
Lys Arg Thr Ser Lys Asp Lys Ser Ser Thr Glu Glu Lys Phe Asn Glu
             115                 120                 125

AAA GGC GAA TTA GTT GAA AAA ATA ATG GCA AGA GCA AAC GGA ACC ATA     432
Lys Gly Glu Leu Val Glu Lys Ile Met Ala Arg Ala Asn Gly Thr Ile
         130                 135                 140
```

```
CTT GAA TAC ACA GGA ATT AAA AGC GAT GGA TCC GGA AAA GCT AAA GAA      480
Leu Glu Tyr Thr Gly Ile Lys Ser Asp Gly Ser Gly Lys Ala Lys Glu
145                 150                 155                 160

ACT TTA AAA GAA TAT GTT CTT GAA GGA ACT CTA ACT GCT GAA AAA GCA      528
Thr Leu Lys Glu Tyr Val Leu Glu Gly Thr Leu Thr Ala Glu Lys Ala
                165                 170                 175

ACA TTG GTG GTT AAA GAA GGA ACT GTT ACT TTA AGT AAG CAC ATT TCA      576
Thr Leu Val Val Lys Glu Gly Thr Val Thr Leu Ser Lys His Ile Ser
            180                 185                 190

AAA TCT GGA GAA GTA ACA GCT GAA CTT AAT GAC ACT GAC AGT ACT CAA      624
Lys Ser Gly Glu Val Thr Ala Glu Leu Asn Asp Thr Asp Ser Thr Gln
        195                 200                 205

GCT ACT AAA AAA ACT GGG AAA TGG GAT GCA GGC ACT TCA ACT TTA ACA      672
Ala Thr Lys Lys Thr Gly Lys Trp Asp Ala Gly Thr Ser Thr Leu Thr
    210                 215                 220

ATT ACT GTA AAC AAC AAA AAA ACT AAA GCC CTT GTA TTT ACA AAA CAA      720
Ile Thr Val Asn Asn Lys Lys Thr Lys Ala Leu Val Phe Thr Lys Gln
225                 230                 235                 240

GAC ACA ATT ACA TCA CAA AAA TAC GAC TCA GCA GGA ACC AAC TTG GAA      768
Asp Thr Ile Thr Ser Gln Lys Tyr Asp Ser Ala Gly Thr Asn Leu Glu
                245                 250                 255

GGC ACA GCA GTC GAA ATT AAA ACA CTT GAT GAA ATT AAA AAC GCT TTA      816
Gly Thr Ala Val Glu Ile Lys Thr Leu Asp Glu Ile Lys Asn Ala Leu
            260                 265                 270

GAA                                                                  819
Glu (2) INFORMATION FOR SEQ ID NO:10:

(i) SEQUENCE CHARACTERISTICS:
        (A) LENGTH: 273 amino acids
        (B) TYPE: amino acid
        (D) TOPOLOGY: linear (ii) MOLECULE TYPE: protein (xi) SEQUENCE DESCRIPTION: SEQ ID NO:10:

Met Lys Lys Tyr Leu Leu Gly Ile Gly Leu Ile Leu Ala Leu Ile Ala
1               5                   10                  15

Cys Lys Gln Asn Val Ser Ser Leu Asp Glu Lys Asn Ser Val Ser Val
                20                  25                  30

Asp Leu Pro Gly Glu Met Lys Val Leu Val Ser Lys Glu Lys Asp Lys
            35                  40                  45

Asp Gly Lys Tyr Ser Leu Met Ala Thr Val Asp Lys Leu Glu Leu Lys
        50                  55                  60

Gly Thr Ser Asp Lys Asn Asn Gly Ser Gly Val Leu Glu Gly Val Lys
65                  70                  75                  80

Ala Asp Lys Ser Lys Val Lys Leu Thr Val Ser Asp Asp Leu Ser Thr
                85                  90                  95

Thr Thr Leu Glu Val Leu Lys Glu Asp Gly Lys Thr Leu Val Ser Lys
            100                 105                 110

Lys Arg Thr Ser Lys Asp Lys Ser Ser Thr Glu Glu Lys Phe Asn Glu
        115                 120                 125

Lys Gly Glu Leu Val Glu Lys Ile Met Ala Arg Ala Asn Gly Thr Ile
    130                 135                 140

Leu Glu Tyr Thr Gly Ile Lys Ser Asp Gly Ser Gly Lys Ala Lys Glu
145                 150                 155                 160

Thr Leu Lys Glu Tyr Val Leu Glu Gly Thr Leu Thr Ala Glu Lys Ala
                165                 170                 175
```

```
Thr Leu Val Val Lys Glu Gly Thr Val Thr Leu Ser Lys His Ile Ser
            180                 185                 190

Lys Ser Gly Glu Val Thr Ala Glu Leu Asn Asp Thr Asp Ser Thr Gln
            195                 200                 205

Ala Thr Lys Lys Thr Gly Lys Trp Asp Ala Gly Thr Ser Thr Leu Thr
            210                 215                 220

Ile Thr Val Asn Asn Lys Lys Thr Lys Ala Leu Val Phe Thr Lys Gln
225                 230                 235                 240

Asp Thr Ile Thr Ser Gln Lys Tyr Asp Ser Ala Gly Thr Asn Leu Glu
                    245                 250                 255

Gly Thr Ala Val Glu Ile Lys Thr Leu Asp Glu Ile Lys Asn Ala Leu
                    260                 265                 270

Glu (2) INFORMATION FOR SEQ ID NO:11:

(i) SEQUENCE CHARACTERISTICS:
        (A) LENGTH: 296 amino acids
        (B) TYPE: amino acid
        (C) STRANDEDNESS: single
        (D) TOPOLOGY: linear (xi) SEQUENCE DESCRIPTION: SEQ ID NO:11:

Met Arg Leu Leu Ile Gly Phe Ala Leu Ala Leu Ala Leu Ile Gly Cys
1               5                   10                  15

Ala Gln Lys Gly Ala Glu Ser Ile Gly Ser Gln Lys Glu Asn Asp Leu
                20                  25                  30

Asn Leu Glu Asp Ser Ser Lys Lys Ser His Gln Asn Ala Lys Gln Asp
                35                  40                  45

Leu Pro Ala Val Thr Glu Asp Ser Val Ser Leu Phe Asn Gly Asn Lys
50                  55                  60

Ile Phe Val Ser Lys Glu Lys Asn Ser Ser Gly Lys Tyr Asp Leu Arg
65                  70                  75                  80

Ala Thr Ile Asp Gln Val Glu Leu Lys Gly Thr Ser Asp Lys Asn Asn
                85                  90                  95

Gly Ser Gly Thr Leu Glu Gly Ser Lys Pro Asp Lys Ser Lys Val Lys
                100                 105                 110

Leu Thr Val Ser Ala Asp Leu Asn Thr Val Thr Leu Glu Ala Phe Asp
            115                 120                 125

Ala Ser Asn Gln Lys Ile Ser Ser Lys Val Thr Lys Lys Gln Gly Ser
            130                 135                 140

Ile Thr Glu Glu Thr Leu Lys Ala Asn Lys Leu Asp Ser Lys Lys Leu
145                 150                 155                 160

Thr Arg Ser Asn Gly Thr Thr Leu Glu Tyr Ser Gln Ile Thr Asp Ala
                165                 170                 175

Asp Asn Ala Thr Lys Ala Val Glu Thr Leu Lys Asn Ser Ile Lys Leu
            180                 185                 190

Glu Gly Ser Leu Val Val Gly Lys Thr Thr Val Glu Ile Lys Glu Gly
            195                 200                 205

Thr Val Thr Leu Lys Arg Glu Ile Glu Lys Asp Gly Lys Val Lys Val
            210                 215                 220

Phe Leu Asn Asp Thr Ala Gly Ser Asn Lys Lys Thr Gly Lys Trp Glu
225                 230                 235                 240

Asp Ser Thr Ser Thr Leu Thr Ile Ser Ala Asp Ser Lys Lys Thr Lys
                245                 250                 255
```

-continued

```
Asp Leu Val Phe Leu Thr Asp Gly Thr Ile Thr Val Gln Gln Tyr Asn
            260                 265                 270

Thr Ala Gly Thr Ser Leu Glu Gly Ser Ala Ser Glu Ile Lys Asn Leu
            275                 280                 285

Ser Glu Leu Lys Asn Ala Leu Lys
    290                 295
```